US012076326B2

(12) United States Patent
Taulelle et al.

(10) Patent No.: US 12,076,326 B2
(45) Date of Patent: *Sep. 3, 2024

(54) CRYSTALLINE FORMS OF A RYANODINE RECEPTOR MODULATOR AND USES THEREOF

(71) Applicant: ARMGO Pharma, Inc., Ardsley, NY (US)

(72) Inventors: Pascal Taulelle, Le Havre (FR); Sandro Belvedere, New York, NY (US)

(73) Assignee: ARMGO Pharma, Inc., Ardsley, NY (US)

( * ) Notice: Subject to any disclaimer, the term of this patent is extended or adjusted under 35 U.S.C. 154(b) by 23 days.

This patent is subject to a terminal disclaimer.

(21) Appl. No.: 17/967,301

(22) Filed: Oct. 17, 2022

(65) Prior Publication Data

US 2023/0075141 A1   Mar. 9, 2023

Related U.S. Application Data

(63) Continuation of application No. 17/571,038, filed on Jan. 7, 2022, now Pat. No. 11,504,383.

(60) Provisional application No. 63/135,083, filed on Jan. 8, 2021.

(51) Int. Cl.
    C07D 281/10    (2006.01)
    A61K 31/554    (2006.01)
    A61P 9/00      (2006.01)
    A61P 21/00     (2006.01)

(52) U.S. Cl.
    CPC .................................. *A61K 31/554* (2013.01)

(58) Field of Classification Search
    CPC ....... C07D 281/10; A61K 31/554; A61P 9/00; A61P 21/00
    See application file for complete search history.

(56) References Cited

U.S. PATENT DOCUMENTS

| | | | |
|---|---|---|---|
| 4,775,536 A | 10/1988 | Patell | |
| 5,580,866 A | 12/1996 | Housley et al. | |
| 8,022,058 B2 | 9/2011 | Marks et al. | |
| 8,618,282 B2 | 12/2013 | Deng et al. | |
| 8,710,045 B2 | 4/2014 | Marks et al. | |
| 8,853,198 B2 | 10/2014 | Yan et al. | |
| 11,504,383 B2 * | 11/2022 | Taulelle | A61K 31/554 |
| 2003/0216376 A1 | 11/2003 | Lifshitz-Liron et al. | |
| 2014/0088171 A1 | 3/2014 | Yan et al. | |
| 2016/0207893 A1 | 7/2016 | Kelly et al. | |

FOREIGN PATENT DOCUMENTS

| | | | |
|---|---|---|---|
| WO | WO-2007024717 A2 | 3/2007 | |
| WO | WO-2008021432 A2 | 2/2008 | |
| WO | WO-2008021439 A2 | 2/2008 | |
| WO | WO-2008060332 A2 | 5/2008 | |
| WO | WO-2008144483 A2 | 11/2008 | |
| WO | WO-2012037105 A1 | 3/2012 | |
| WO | WO-2013156505 A1 | 10/2013 | |

OTHER PUBLICATIONS

ACC15 Booklet, "We See Strength . . . ", Connect 2015 Annual Conference, Parent Project Muscular Dystrophy.
Andersson, et al. Ryanodine receptor oxidation causes intracellular calcium leak and muscle weakness in aging. Cell Metabolism. Aug. 2011;14(2):196-207. DOI: 10.1016/j.cmet.2011.05.014. PMID: 21803290; PMCID: PMC3690519.
Barthélémy et al. Targeting RyR Activity Boosts Antisense Exon 44 and 45 Skipping in Human DMD Skeletal or Cardiac Muscle Culture Models. Mol Ther Nucleic Acids. Dec. 6, 2019;18:580-589.
Blat et al. Drug Discovery of Therapies for Duchenne Muscular Dystrophy. J Biomol Screen. Dec. 2015;20(10):1189-203. doi: 10.1177/1087057115586535. Epub May 14, 2015. PMID: 25975656.
Capogrosso et al. Ryanodine channel complex stabilizer compound S48168/ARM210 as a disease modifier in dystrophin-deficient mdx mice: proof-of-concept study and independent validation of efficacy. FASEB J. Feb. 2018;32(2):1025-1043.
Deng et al., Organic Process Research & Development 2017 21 (11), 1801-1805.
Francis et al., Catecholaminergic polymorphic ventricular tachycardia, Heart Rhythm, vol. 2, Issue 5,2005, pp. 550-554,ISSN 1547-5271, https://doi.org/10.1016/j.hrthm.2005.01.024.
International Search Report and Written Opinion issued in PCT/US2021/059572 on Mar. 16, 2022.
International Search Report and Written Opinion issued in PCT/US2022/011640 on May 18, 2022.
J.J. Todd et al., LBP.15 Safety, pharmacokinetics, and preliminary efficacy of Rycal S 48168 (ARM210) for RYR1-related myopathies: a phase one, open-label dose-escalation trial (Abstract). 2021.
J.J. Todd et al., LBP.15 Safety, pharmacokinetics, and preliminary efficacy of Rycal S 48168 (ARM210) for RYR1-related myopathies: a phase one, open-label dose-escalation trial (Poster). 2021.
János Szabó, Gábor Bernáth, Ágnes Katócs, Lajos Fodor, and Pál Sohár. Synthesis and spectroscopic investigations of 1,4-benzothiazepine derivatives. Canadian Journal of Chemistry. 65(1): 175-181. https://doi.org/10.1139/v87-027. 1987.
Katritzky et al., 1H and 13C NMR study of tetrahydro-1,4-benzothiazepine conformations, J. Chem. Soc., Perkin Trans. 2, 2002, pp. 1816-1822.
Katritzky et al., Convenient syntheses of 2,3,4,5-tetrahydro-1,4-benzothiazepines, -1, 4-benzoxazepines and -1,4-benzodiazepines, J. Chem. Soc., Perkin Trans. 1, 2002, 592-598.
Kushnir et al., Intracellular calcium leak as a therapeutic target for RYR1-related myopathies. Acta Neuropathol. Jun. 2020;139(6):1089-1104. doi: 10.1007/s00401-020-02150-w. Epub Mar. 31, 2020. PMID: 32236737; PMCID: PMC7788518.

(Continued)

*Primary Examiner* — Brenda L Coleman
(74) *Attorney, Agent, or Firm* — Wilson Sonsini Goodrich & Rosati

(57) ABSTRACT

The present disclosure relates to crystalline forms of the compound 4-[(7-methoxy-2,3-dihydro-1,4-benzothiazepin-4(5H)yl)methyl]benzoic acid hemifumarate, pharmaceutical compositions comprising these compounds and uses thereof to treat diseases and conditions associated with Ryanodine Receptor (RyR) dysfunction, in particular cardiac and musculoskeletal disorders and diseases.

25 Claims, 11 Drawing Sheets

(56) References Cited

OTHER PUBLICATIONS

Nair et al., Synthesis & Reactions of Benz[I,4] thiazepine Derivatives, Indian Journal of Chemistry, vol. 7, Sep. 1969, pp. 862-865.
Non-Final Office Action issued in U.S. Appl. No. 14/076,474, filed Feb. 3, 2014.
Orphan Drug Designations and Approvals, 4-[(7-Methoxy-2,3-dihydro-1,4-benzothiazepin-4(5H)-yl)methyl]benzoic acid, hemifumarate, Aug. 17, 2018.
Orphan Drug Designations and Approvals, 4-[(7-Methoxy-2,3-dihydro-1,4-benzothiazepin-4(5H)-yl)methyl]benzoic acid, hemifumarate, May 5, 2020.
Orphan Drug Designations and Approvals, 4-[(7-Methoxy-2,3-dihydro-1,4-benzothiazepin-4(5H)-yl)methyl]benzoic acid, hemifumarate, Nov. 18, 2015.
Pindeleska et al., Pharmaceuticals Cocrystals, slats and Polymorphs: Advanced Characterization Techniques, Advanced Drug Delivery Reviews, 2017, vol. 117, pp. 111-146.
Popp et al., Development of Selective CBP/P300 Benzoxazepine Bromodomain Inhibitors, Journal of Medicinal Chemistry, Sep. 27, 2016, vol. 59, pp. 8889-8912.
Pubmed Compound Record for CID 122427851, '4, 7-dimethyl-3,5-dihydro-2H-1,4-benzothizepine, U.S. National Library of Medicine, Dec. 8, 2016, pp. 1-8.
Roston et al. The clinical and genetic spectrum of catecholaminergic polymorphic ventricular tachycardia: findings from an international multicentre registry. Europace. Mar. 1, 2018;20(3):541-547. doi: 10.1093/europace/euw389. PMID: 28158428; PMCID: PMC6059141.
S 48168 (ARM 210) for the Treatment of RYR1-related Myopathies (RYR1-RM), NCT04141670, ClinicalTrials,gov. 2021.
Snorek et al., PQRI Recommendations on Particle Size Analysis of Drug Substances Used in Oral Dosage Forms, Journal of Pharmaceutical Sciences, 2007, vol. 96, pp. 1451-1467.
Szabo et al., Synthesis and Transformations of 4,5-Dihydro-1,4-benzothiazepin-3(2H)-one Derivatives1,2), Chem. Ber. 119, 2004-2913 (1986).
Tester et al., Identification of a Novel Homozygous Multi-Exon Duplication in RYR2 Among Children With Exertion-Related Unexplained Sudden Deaths in the Amish Community. JAMA Cardiol. Mar. 1, 2020;5(3):13-18. doi: 10.1001/jamacardio.2019.5400. PMID: 31913406; PMCID: PMC6990654.
Treatment of an Inherited Ventricular Arrhythmia, NCT05122975, ClinicalTrials, gov. 2021.
Zheng et al., Discovery of Ziresovir as a Potent, Selective, and Orally Bioavailable Respiratory Syncytial Virus Fusion Protein Inhibitor, Journal of Medicinal Chemistry, Jun. 13, 2019, vol. 62, pp. 6003-6014.

* cited by examiner

US 12,076,326 B2

CRYSTALLINE FORMS OF A RYANODINE RECEPTOR MODULATOR AND USES THEREOF

CROSS-REFERENCE

This application is a continuation of U.S. application Ser. No. 17/571,038, filed Jan. 7, 2022, which claims the benefit of U.S. Provisional Application No. 63/135,083, filed Jan. 8, 2021, each of which is incorporated herein by reference in its entirety.

BACKGROUND

The sarcoplasmic reticulum (SR) is a structure in cells that functions, among other things, as a specialized intracellular calcium ($Ca^{2+}$) store. Ryanodine receptors (RyRs) are channels in the SR that open and close to regulate the release of $Ca^{2+}$ from the SR into the intracellular cytoplasm of the cell. Release of $Ca^{2+}$ into the cytoplasm from the SR increases cytoplasmic $Ca^{2+}$ concentration. Open probability of RyRs refers to the likelihood that a RyR is open at any given moment, and therefore capable of releasing $Ca^{2+}$ into the cytoplasm from the SR. Three RyR isoforms are known. RyR1 is the predominant isoform expressed in mammalian skeletal muscle, and is predominantly found in cardiac muscle, whereas RyR3 expression is low in skeletal muscle.

$Ca^{2+}$ release from the SR is modulated by several RyR binding proteins. Calstabin1 (FKBP12) and calstabin2 (FKBP12.6) stabilize the closed state of the RyR1 and RyR2, respectively. Mutations in RYR1 or RYR2 are characterized by reduced binding of Calstabin 1 or Calstabin2, respectively, and inappropriate channel opening not related to contraction signals. This channel opening is further exacerbated by post-translational modifications such as PKA-phosphorylation, oxidation, or nitrosylation of the RyR channel. The resulting dissociation of Calstabin can lead to leaky channels, which exhibit a pathologic increase in the open probability under resting conditions. The SR $Ca^{2+}$ leak leads to a reduction in SR $Ca^{2+}$ content, with less $Ca^{2+}$ available for release and consequently weaker muscle contractions.

SUMMARY

In some embodiments, the present disclosure provides a composition comprising a crystalline form of 4-[(7-methoxy-2,3-dihydro-1,4-benzothiazepin-4(5H)yl)methyl] benzoic acid hemifumarate, wherein if a melting point of the crystalline form is obtained by: (a) equilibrating a sample of said crystalline form at a temperature of about 20° C. in a temperature-controlled chamber; and (b) increasing the temperature of the temperature-controlled chamber at about 10° C./minute to 250° C. using a differential scanning calorimetry instrument, then a melting point of 208-210° C. ($T_{onset}$) is obtained.

In some embodiments, the present disclosure provides a composition comprising a crystalline form of 4-[(7-methoxy-2,3-dihydro-1,4-benzothiazepin-4(5H)yl)methyl] benzoic acid hemifumarate for use in a method of treating a condition, wherein if a melting point of the crystalline form is obtained by: (a) equilibrating a sample of said crystalline form at a temperature of about 20° C. in a temperature-controlled chamber; and (b) increasing the temperature of the temperature-controlled chamber at about 10° C./minute to 250° C. using a differential scanning calorimetry instrument, then a melting point of 208-210° C. ($T_{onset}$) is obtained.

In some embodiments, the present disclosure provides a composition comprising a crystalline form of 4-[(7-methoxy-2,3-dihydro-1,4-benzothiazepin-4(5H)yl)methyl] benzoic acid hemifumarate, wherein if a melting point of the crystalline form is obtained by: (a) equilibrating a sample of said crystalline form at a temperature of about 20° C. in a temperature-controlled chamber; and (b) increasing the temperature of the temperature-controlled chamber at a scan rate of about 10° C./minute to 250° C. using a differential scanning calorimetry instrument, then a melting point of 201-203° C. ($T_{onset}$) is obtained.

In some embodiments, the present disclosure provides a composition comprising a crystalline form of 4-[(7-methoxy-2,3-dihydro-1,4-benzothiazepin-4(5H)yl)methyl] benzoic acid hemifumarate, for use in a method of treating a condition, wherein if a melting point of the crystalline form is obtained by (a) equilibrating a sample of said crystalline form at a temperature of about 20° C. in a temperature-controlled chamber; and (b) increasing the temperature of the temperature-controlled chamber at about 10° C./minute to 250° C. using a differential scanning calorimetry instrument, then a melting point of 201-203° C. ($T_{onset}$) is obtained.

In some embodiments, the present disclosure provides a method of treating a condition, comprising administering to a subject in need thereof a therapeutically-effective amount of a composition, the composition comprising a crystalline form of 4-[(7-methoxy-2,3-dihydro-1,4-benzothiazepin-4 (5H)yl)methyl]benzoic acid hemifumarate.

(5H)yl)methyl]benzoic acid hemifumarate Form 2 at inception (top panel) and after 3, 6, 12 and 24 months.

Figure 11:
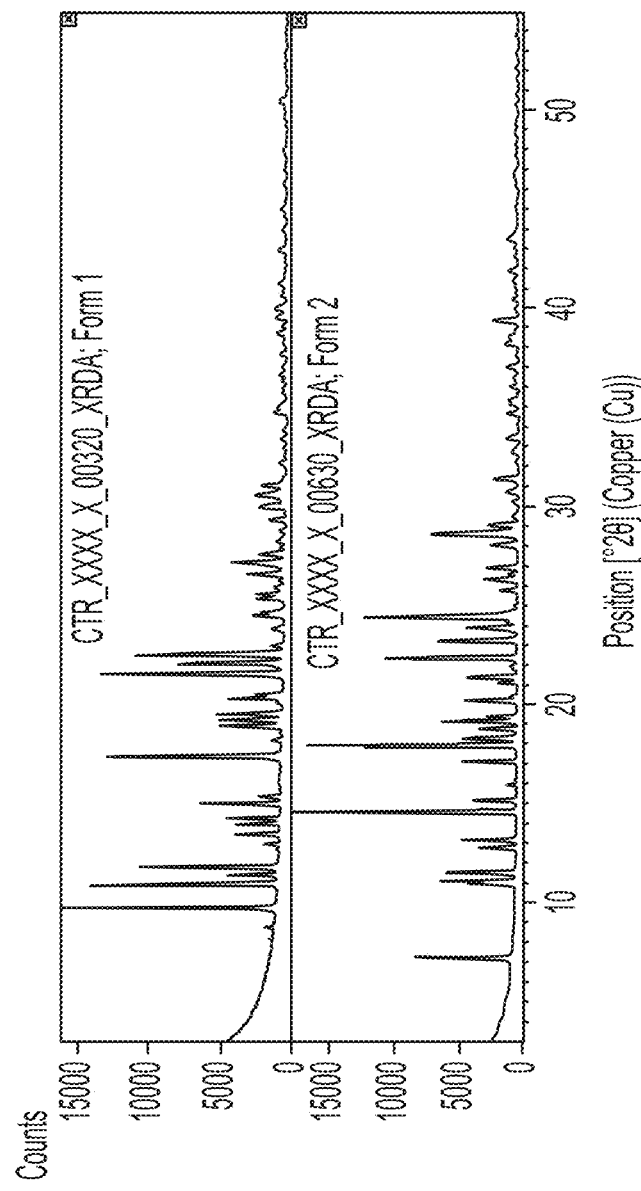

FIG. 11 depicts a comparison of the X-ray diffraction (XRD) patterns of 4-[(7-methoxy-2,3-dihydro-1,4-benzothiazepin-4(5H)yl)methyl]benzoic acid hemifumarate Form 1 (top panel) and Form 2 (bottom panel).

DETAILED DESCRIPTION

The present disclosure provides polymorphic forms of 4-[(7-methoxy-2,3-dihydro-1,4-benzothiazepin-4(5H)yl) methyl]benzoic acid, hemifumarate (Compound I), pharmaceutical compositions comprising same, methods for preparation thereof, and use thereof in treating conditions associated with RyRs, including, for example, cardiac disorder or disease, a musculoskeletal disorder or disease, cancer associated muscle weakness, malignant hyperthermia, and diabetes.

Described herein are polymorphic forms of 4-[(7-methoxy-2,3-dihydro-1,4-benzothiazepin-4(5H)yl)methyl] benzoic acid, hemifumarate (Compound I) having beneficial properties. For example, Compound I polymorphs can be stable in a closed glass container for at least 24 months in storage conditions of −18° C., and 25° C./60% relative humidity (RH). For example, Compound I polymorphs can be stable in a closed glass container for at least 12 months at 30° C./65% relative humidity (RH). For example, Compound I polymorphs can be stable in a closed glass container for at least 6 months at 40° C./75% relative humidity (RH).

The polymorphs described herein include, for example, Rycals. Rycals are small molecules that function as $Ca^{2+}$ channel stabilizers. The polymorphs are useful for treating conditions, disorders, and diseases associated with leaky Ryanodine Receptor (RyRs). Non-limiting examples of such conditions include a cardiac condition, a musculoskeletal condition, cancer associated muscle weakness, malignant hyperthermia, and diabetes.

Polymorphs are distinct solid state phases of a given chemical compound that possess different arrangements and/or conformations of the molecules. Polymorphism is the ability of a substance to exist in more than one distinct amorphous and crystalline forms. In some embodiments, the polymorphic forms disclosed herein are substantially anhydrous. In some embodiments, the polymorphic forms disclosed herein are stable up to at least 6 months at high humidity conditions (75% RH), and for at least 24 months at ambient conditions 25° C./60% relative humidity (RH). The polymorphic forms are suitable for preparation of pharmaceutical compositions for the treatment of RyR-associated conditions.

The present disclosure provides two polymorphic forms of 4-[(7-methoxy-2,3-dihydro-1,4-benzothiazepin-4(5H)yl) methyl]benzoic acid, hemifumarate of formula (I), designated Form 1 and Form 2. In some embodiments, the polymorphs are crystalline. In some embodiments, the polymorphs are anhydrous. In some embodiments, the polymorphs are substantially anhydrous.

The compound of formula (I) has an empirical formula possessing the following structure or an ionized form thereof:

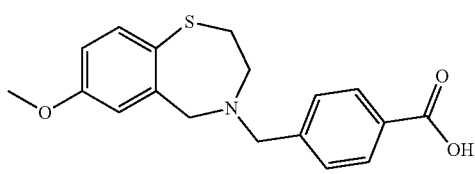

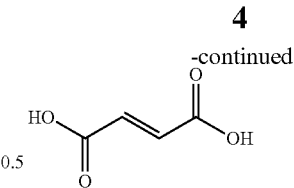

For example, a compound of formula (I) can be in ionized form, comprising two ionized molecules of 4-[(7-methoxy-2,3-dihydro-1,4-benzothiazepin-4(5H)yl)methyl]benzoic acid.

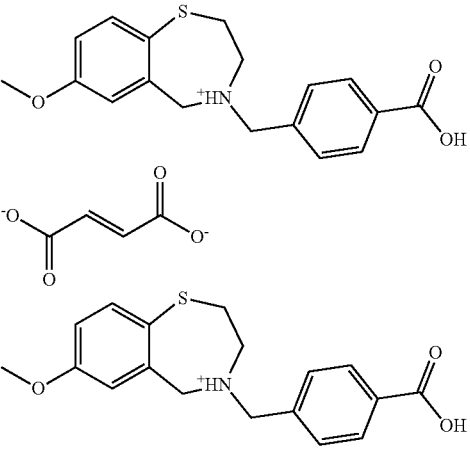

4-[(7-methoxy-2,3-dihydro-1,4-benzothiazepin-4(5H)yl) methyl]benzoic acid, hemifumarate Form 1

Provided herein is a crystalline 4-[(7-methoxy-2,3-dihydro-1,4-benzothiazepin-4(5H)yl)methyl]benzoic acid, hemifumarate, Form 1. Further provided herein is a composition comprising a crystalline 4-[(7-methoxy-2,3-dihydro-1,4-benzothiazepin-4(5H)yl)methyl]benzoic acid, hemifumarate, Form 1.

In some embodiments, the crystalline form is an anhydrous and slightly hygroscopic crystalline form. The crystalline form exhibits a melting point at 201-203° C. ($T_{onset}$). In some embodiments, the crystalline form is an anhydrous and non-hygroscopic crystalline form with a melting point at 201.4° C. ($T_{onset}$) with a $T_{peak}$ of 202.6° C. (melting/degradation). Based on the loss of mass observed by TGA analysis, the melting can be accompanied by immediate degradation.

In some embodiments, provided herein is a composition comprising a crystalline 4-[(7-methoxy-2,3-dihydro-1,4-benzothiazepin-4(5H)yl)methyl]benzoic acid, hemifumarate, wherein if an X-ray diffraction pattern of the crystalline form is obtained using measurement conditions, the measurement conditions comprising:

| | |
|---|---|
| Start Position [° 2θ] | 3.00 |
| End Position [° 2θ] | 54.99 |
| Step Size [° 2θ] | 0.018 |
| Scan Step Time [s] | 34.92 |
| Measurement Temperature [° C.] | 25.00 |
| K-Alpha1 [Å] | 1.54 |
| K-Alpha2 [Å] | 1.54 |
| K-Beta [Å] | 1.39 |
| Spinning | Yes | then at least two X-ray diffraction peaks selected from 9.8±0.1, 11.8±0.1, 13.5±0.1, 14.0±0.1, 14.3±0.1, 17.4±0.1, 18.9±0.1, 19.6±0.1, 22.1±0.1, 26.6±0.1, and 27.2±0.1 degrees two theta (°θ) are observed.

In some embodiments, if an X-ray diffraction pattern of the crystalline form is obtained using the above measurement conditions, X-ray diffraction peaks at 9.8±0.1, 11.0±0.1, 17.4±0.1, 21.6±0.1 and 22.6±0.1 degrees two theta (°θ) are observed.

In some embodiments, if an X-ray diffraction pattern of the crystalline form is obtained using the above measurement conditions, X-ray diffraction peaks at 9.8±0.1, 11.0±0.1, 11.8±0.1, 15.0±0.1, 17.4±0.1, 21.6±0.1, 22.1±0.1, and 22.6±0.1 degrees two theta (°θ) are observed.

In some embodiments, if an X-ray diffraction pattern of the crystalline form is obtained using the above measurement conditions, X-ray diffraction peaks at 9.8±0.1, 11.0±0.1, 11.4±0.1, 11.8±0.1, 13.5±0.1, 14.0±0.1, 14.3±0.1, 15.0±0.1, 17.4±0.1, 18.9±0.1, 19.3±0.1, 19.6±0.1, 20.3±0.1, 21.6±0.1, 22.1±0.1, 22.6±0.1, 26.6±0.1, and 27.2±0.1 degrees two theta (°θ) are observed.

Figure 1:
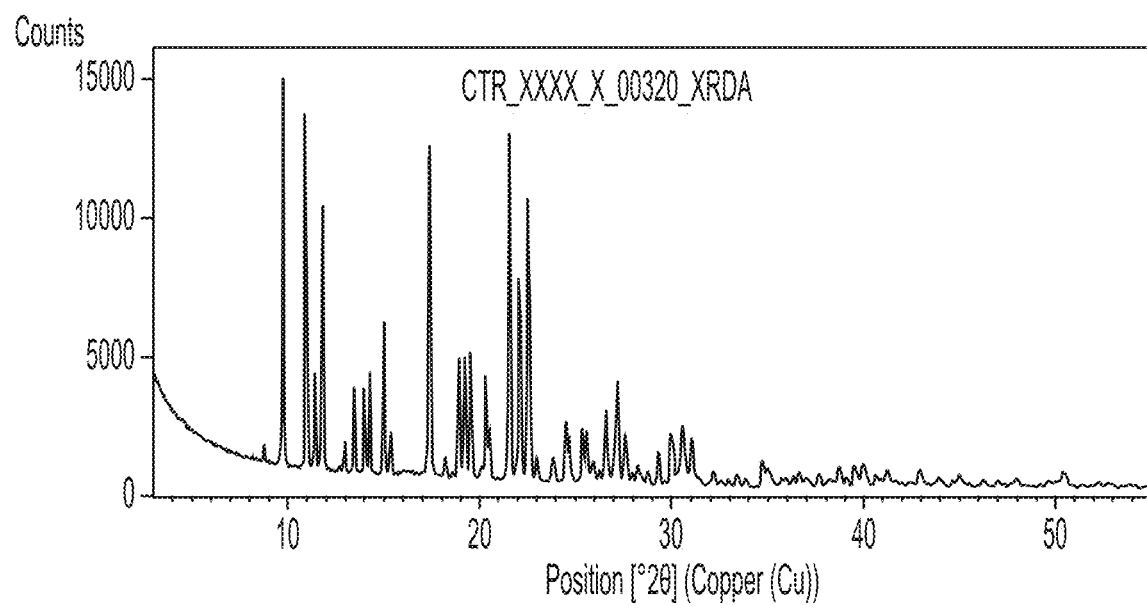
FIG. 1 depicts a characteristic X-ray diffraction (XRD) pattern of 4-[(7-methoxy-2,3-dihydro-1,4-benzothiazepin-4 (5H)yl)methyl]benzoic acid hemifumarate Form 1.

In some embodiments, if an X-ray diffraction pattern of the crystalline form is obtained using the above measurement conditions, X-ray diffraction peaks substantially as shown in FIG. 1 are observed.

In some embodiments, the X-ray diffraction (XRD) pattern of form 2 comprises at least two diffraction peaks selected from 9.8±0.1, 11.8±0.1, 13.5±0.1, 14.0±0.1, 14.3±0.1, 17.4±0.1, 18.9±0.1, 19.6±0.1, 22.1±0.1, 26.6±0.1, and 27.2±0.1 degrees two theta (°θ). In some embodiments, the X-ray diffraction (XRD) pattern comprises at least three diffraction peaks selected from 9.8±0.1, 11.8±0.1, 13.5±0.1, 14.0±0.1, 14.3±0.1, 17.4±0.1, 18.9±0.1, 19.6±0.1, 22.1±0.1, 26.6±0.1, and 27.2±0.1 degrees two theta (°θ). In some embodiments, the X-ray diffraction (XRD) pattern comprises at least four diffraction peaks selected from 9.8±0.1, 11.8±0.1, 13.5±0.1, 14.0±0.1, 14.3±0.1, 17.4±0.1, 18.9±0.1, 19.6±0.1, 22.1±0.1, 26.6±0.1, and 27.2±0.1 degrees two theta (°θ). In some embodiments, the X-ray diffraction (XRD) pattern comprises at least five diffraction peaks selected from 9.8±0.1, 11.8±0.1, 13.5±0.1, 14.0±0.1, 14.3±0.1, 17.4±0.1, 18.9±0.1, 19.6±0.1, 22.1±0.1, 26.6±0.1, and 27.2±0.1 degrees two theta (°θ). In some embodiments, the X-ray diffraction pattern comprises a peak at 9.8±0.1 degrees two theta (°θ).

In some embodiments, the crystalline form is characterized by an X-ray diffraction (XRD) pattern comprising diffraction peaks at 9.8±0.1, 11.0±0.1, 17.4±0.1, 21.6±0.1 and 22.6±0.1 degrees two theta (° θ).

In some embodiments, the crystalline form is characterized by an X-ray diffraction (XRD) pattern comprising diffraction peaks at 9.8±0.1, 11.0±0.1, 11.8±0.1, 15.0±0.1, 17.4±0.1, 21.6±0.1, 22.1±0.1, and 22.6±0.1 degrees two theta (°θ).

In some embodiments, the crystalline form is characterized by an X-ray diffraction (XRD) pattern comprising diffraction peaks at 9.8±0.1, 11.0±0.1, 11.4±0.1, 11.8±0.1, 13.5±0.1, 14.0±0.1, 14.3±0.1, 15.0±0.1, 17.4±0.1, 18.9±0.1, 19.3±0.1, 19.6±0.1, 20.3±0.1, 21.6±0.1, 22.1±0.1, 22.6±0.1, 26.6±0.1, and 27.2±0.1 degrees two theta (°θ).

In some embodiments, the crystalline form is characterized by an X-ray diffraction (XRD) pattern substantially as shown in FIG. 1.

In some embodiments, the crystalline form is characterized by an X-ray diffraction (XRD) pattern substantially as shown in TABLE 1.

TABLE 1

XRD peaks of Form 1

| No. | 2-Theta [° 2θ] | Relative Intensity (%) |
|---|---|---|
| 1 | 9.8 | 100.0 |
| 2 | 11.0 | 82.1 |
| 3 | 11.4 | 21.6 |
| 4 | 11.8 | 57.3 |
| 5 | 13.5 | 18.9 |
| 6 | 14.0 | 20.5 |
| 7 | 14.3 | 25.2 |
| 8 | 15.0 | 40.4 |
| 9 | 17.4 | 77.1 |
| 10 | 18.9 | 31.8 |
| 11 | 19.3 | 33.3 |
| 12 | 19.6 | 31.0 |
| 13 | 20.3 | 23.3 |
| 14 | 21.6 | 87.0 |
| 15 | 22.1 | 49.2 |
| 16 | 22.6 | 63.9 |
| 17 | 26.6 | 19.6 |
| 18 | 27.2 | 22.0 |

In some embodiments, provided herein is a composition comprising a crystalline 4-[(7-methoxy-2,3-dihydro-1,4-benzothiazepin-4(5H)yl)methyl]benzoic acid, hemifumarate, wherein, if a melting point of the crystalline form is obtained by (a) equilibrating a sample of said crystalline form at a temperature of about 20° C. in a temperature-controlled chamber; and (b) increasing the temperature of the temperature-controlled chamber at a scan rate of about 10° C./minute to 250° C. using a differential scanning calorimetry instrument, then a melting point of 201-203° C. ($T_{onset}$) is obtained. The differential scanning calorimetry instrument can be, for example, DSC Q1000 or DSC Q2000.

Figure 2:
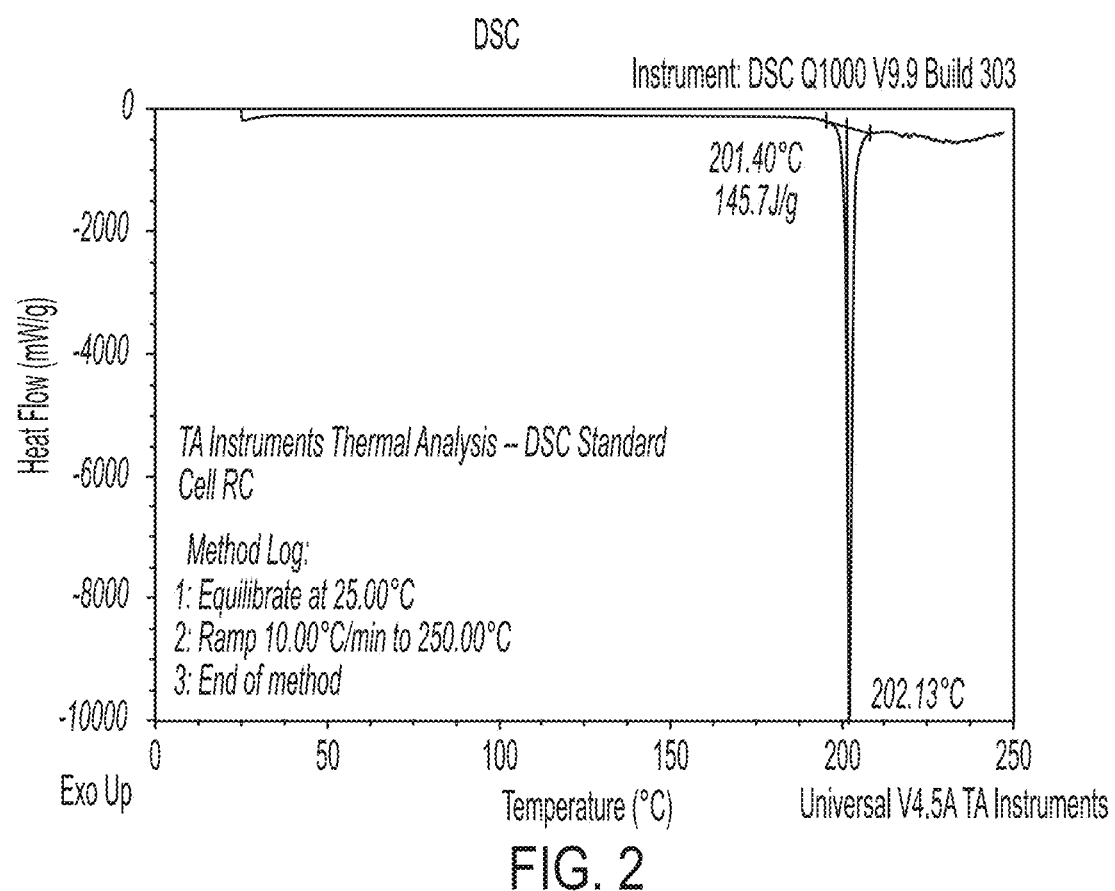
FIG. 2 depicts a characteristic Differential Scanning calorimetry (DSC) profile of 4-[(7-methoxy-2,3-dihydro-1,4-benzothiazepin-4(5H)yl)methyl]benzoic acid hemifumarate Form 1.

In some embodiments, provided herein is a composition comprising a crystalline 4-[(7-methoxy-2,3-dihydro-1,4-benzothiazepin-4(5H)yl)methyl]benzoic acid, hemifumarate, characterized by a differential scanning calorimetry (DSC) profile substantially as shown in FIG. 2. In some embodiments, the crystalline form is characterized by melting point at about 201-203° C. ($T_{onset}$). As shown in FIG. 2, an illustrative sample of the crystalline form has a $T_{onset}$: 201.4° C., $T_{peak}$: 202.6° C. (Melting/degradation).

Figure 3:
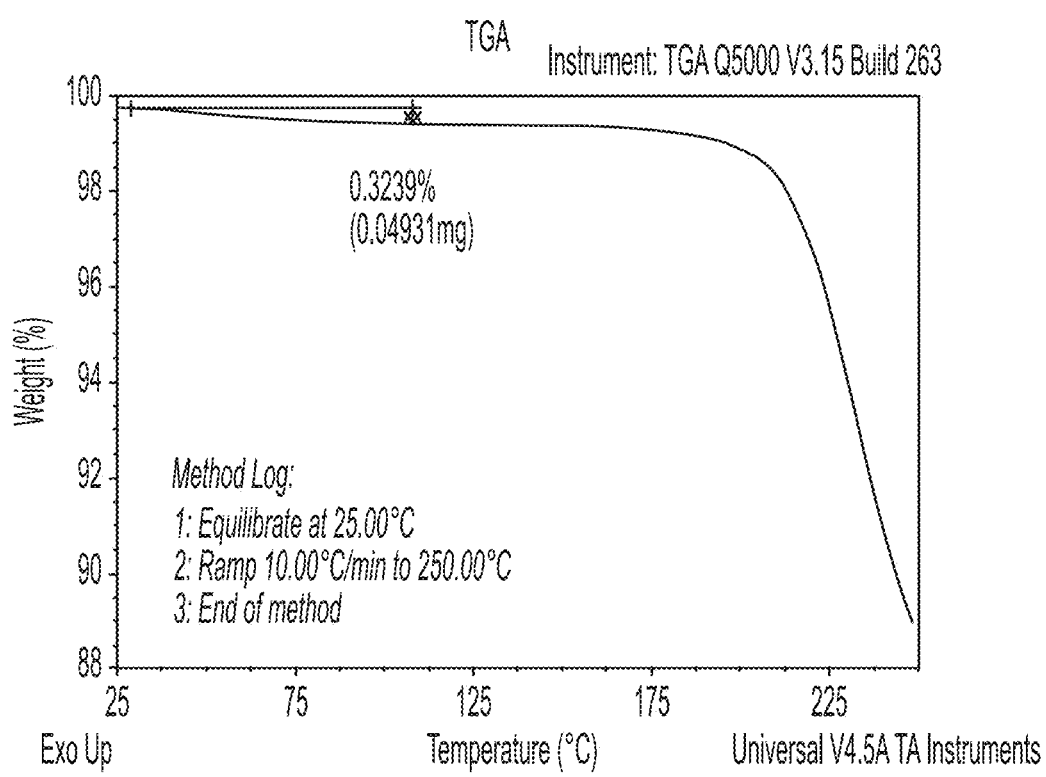
FIG. 3 depicts a characteristic Thermogravimetric analysis (TGA) profile 4-[(7-methoxy-2,3-dihydro-1,4-benzothiazepin-4(5H)yl)methyl]benzoic acid hemifumarate Form 1.

In some embodiments, the crystalline form is further characterized by a thermo gravimetric analysis (TGA) profile. In some embodiments, provided herein is a composition comprising a crystalline 4-[(7-methoxy-2,3-dihydro-1,4-benzothiazepin-4(5H)yl)methyl]benzoic acid, hemifumarate, wherein, if a thermogravimetric analysis of the crystalline form is obtained by: (a) equilibrating a sample of said crystalline form at 25° C. in a temperature-controlled chamber; and (b) increasing the temperature at a scan rate of about 10° C./minute to 250° C. using a thermogravimetric analysis instrument, then a thermogravimetric analysis profile substantially as shown in FIG. 3 is obtained. In some embodiments, the loss of mass before melting degradation is about 1%. The thermogravimetric analysis instrument can be, for example, TGAQ5000.

In some embodiments, provided herein is a composition comprising a crystalline 4-[(7-methoxy-2,3-dihydro-1,4-benzothiazepin-4(5H)yl)methyl]benzoic acid, hemifumarate, wherein the crystalline form is characterized by a thermogravimetric analysis profile substantially as shown in FIG. 3.

In some embodiments, the crystalline form is further characterized by a dynamic vapor sorption (DVS) profile. In some embodiments, provided herein is a composition comprising a crystalline 4-[(7-methoxy-2,3-dihydro-1,4-benzothiazepin-4(5H)yl)methyl]benzoic acid, hemifumarate, wherein, if a dynamic vapor sorption of the crystalline form is obtained by measuring mass variation of said crystalline form as a function of relative humidity using a DVS intrinsic instrument, wherein said measuring comprises: (a) equilibrating a sample of said crystalline form at 25° C. and 50% relative humidity in a temperature-controlled and humidity controlled chamber until mass variation is less than 0.002% per minute for 6 hours; (b) increasing the relative humidity from 50% to 90% at a rate of 10% per hour; (c) equilibrating the sample at 90% relative humidity until mass variation of less than 0.002% per minute for 6 hours is observed; (d) decreasing the relative humidity from 90% to 0% at a rate of 10% per hour; (e) equilibrating the sample at 0% relative humidity until mass variation of less than 0.002% per minute for 6 hours is observed; and (f) increasing the relative humidity from 0% to 50% at a rate of 10% per hour, then a dynamic vapor sorption profile substantially as shown in FIG. 4 is obtained.

Figure 4:
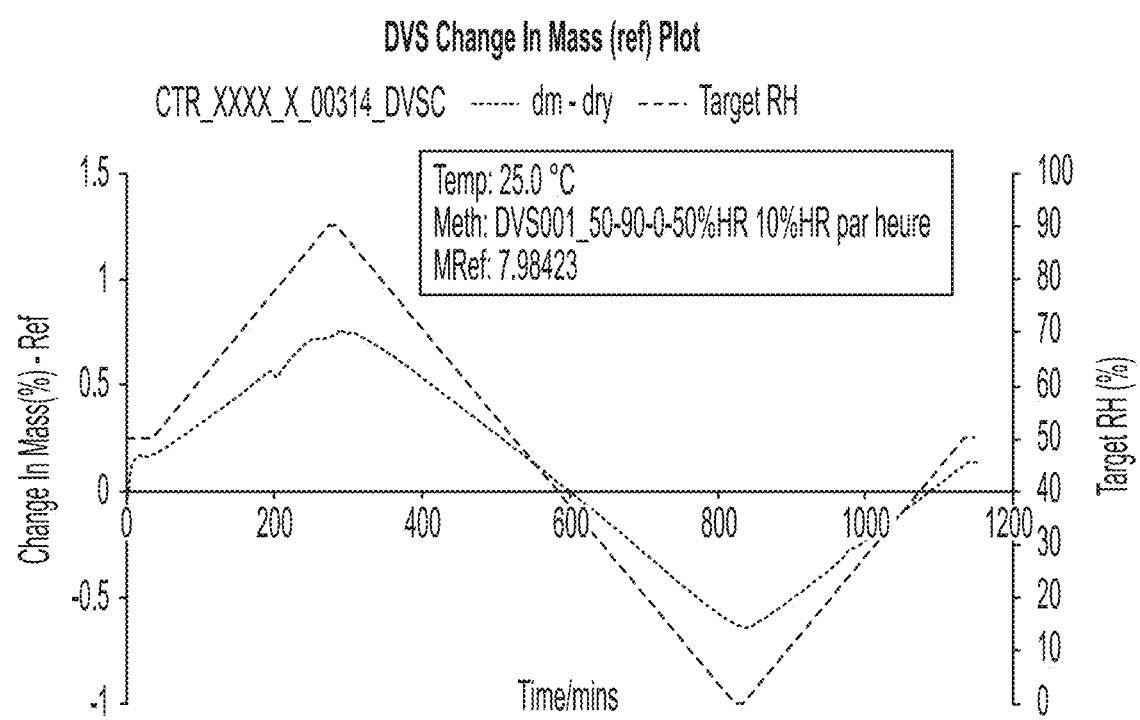
FIG. 4 depicts a characteristic Dynamic Vapor Sorption (DVS) profile of 4-[(7-methoxy-2,3-dihydro-1,4-benzothiazepin-4(5H)yl)methyl]benzoic acid hemifumarate Form 1.

In some embodiments, provided herein is a composition comprising a crystalline 4-[(7-methoxy-2,3-dihydro-1,4-benzothiazepin-4(5H)yl)methyl]benzoic acid, hemifumarate, wherein the crystalline form is characterized by a dynamic vapor sorption profile substantially as shown in FIG. 4.

In some embodiments, the a crystalline 4-[(7-methoxy-2,3-dihydro-1,4-benzothiazepin-4(5H)yl)methyl]benzoic acid, hemifumarate, is anhydrous. In some embodiments, the a crystalline 4-[(7-methoxy-2,3-dihydro-1,4-benzothiazepin-4(5H)yl)methyl]benzoic acid hemifumarate is substantially anhydrous.

4-[(7-methoxy-2,3-dihydro-1,4-benzothiazepin-4(5H)yl) methyl]benzoic acid, hemifumarate Form 2

Provided herein is a crystalline 4-[(7-methoxy-2,3-dihydro-1,4-benzothiazepin-4(5H)yl)methyl]benzoic acid, hemifumarate, Form 2. Provided herein is a composition comprising a crystalline 4-[(7-methoxy-2,3-dihydro-1,4-benzothiazepin-4(5H)yl)methyl]benzoic acid, hemifumarate, Form 2.

In some embodiments, the crystalline form is an anhydrous and non-hygroscopic crystalline form with a melting point at 208-210° C. ($T_{onset}$). In some embodiments, the crystalline form is an anhydrous and non-hygroscopic crystalline form with a melting point at 209.5° C. ($T_{onset}$) with a $T_{peak}$ of 210.7° C. (melting/degradation). Based on the loss of mass observed by TGA analysis, the melting can be accompanied by immediate degradation.

In some embodiments, provided herein is a composition comprising a crystalline 4-[(7-methoxy-2,3-dihydro-1,4-benzothiazepin-4(5H)yl)methyl]benzoic acid, hemifumarate, wherein if an X-ray diffraction pattern (XRD) of the crystalline form is obtained using measurement conditions, the measurement conditions comprising:

| | |
|---|---|
| Start Position [° 2θ] | 3.00 |
| End Position [° 2θ] | 54.99 |
| Step Size [° 2θ] | 0.018 |
| Scan Step Time [s] | 34.92 |
| Measurement Temperature [° C.] | 25.00 |
| K-Alpha1 [Å] | 1.54 |
| K-Alpha2 [Å] | 1.54 |
| K-Beta [Å] | 1.39 |
| Spinning | Yes | then at least two X-ray diffraction peaks selected from 7.3±0.1, 13.2±0.1, 14.6±0.1, 17.1±0.1, 18.0±0.1, 18.3±0.1, 23.2±0.1, 23.9±0.1, 24.4±0.1, and 28.6±0.1 degrees two theta (°θ) are observed.

In some embodiments, if an X-ray diffraction pattern of the crystalline form is obtained using the above measurement conditions, then X-ray diffraction peaks at 7.3±0.1, 14.6±0.1, 18.0±0.1, 22.4±0.1, and 24.4±0.1 degrees two theta (°θ) are observed.

In some embodiments, if an X-ray diffraction pattern of the crystalline form is obtained using the above measurement conditions, then X-ray diffraction peaks at 7.3±0.1, 11.1±0.1, 14.6±0.1, 18.0±0.1, 19.2±0.1, 22.4±0.1, 23.2±0.1, and 24.4±0.1 degrees two theta (°θ) are observed.

In some embodiments, if an X-ray diffraction pattern of the crystalline form is obtained using the above measurement conditions, then X-ray diffraction peaks at 7.3±0.1, 11.0±0.1, 11.1±0.1, 11.5±0.1, 13.2±0.1, 14.6±0.1, 15.2±0.1, 17.1±0.1, 18.0±0.1, 18.3±0.1, 19.2±0.1, 20.2±0.1, 21.4±0.1, 22.4±0.1, 23.2±0.1, 23.9±0.1, 24.4±0.1 and 28.6±0.1 degrees two theta (°θ) are observed.

Figure 6:
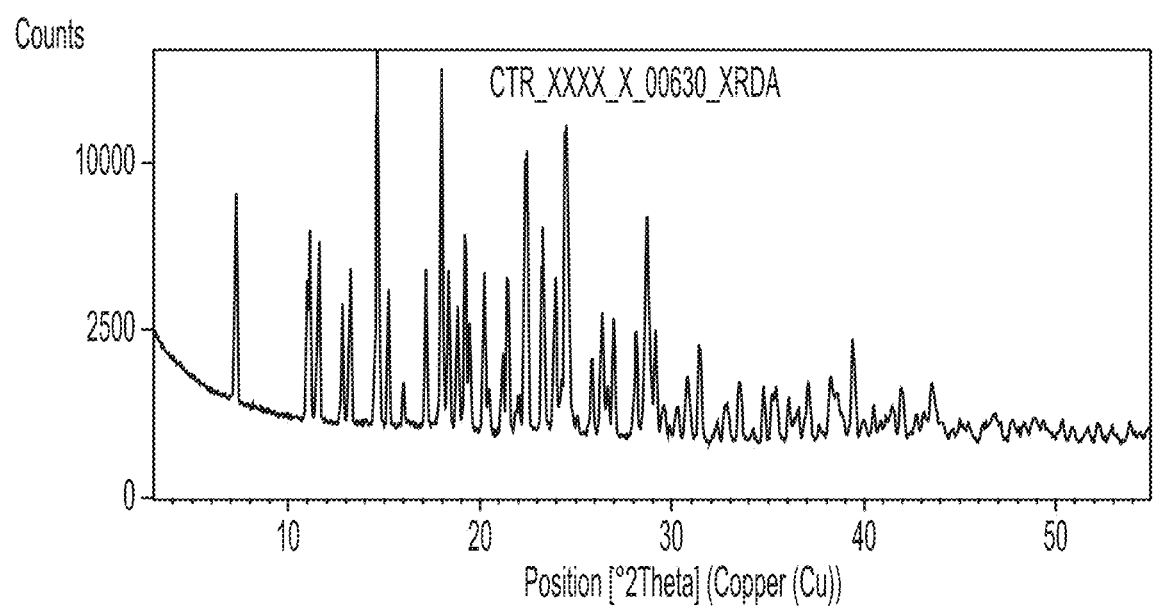
FIG. 6 depicts a characteristic X-ray diffraction (XRD) pattern of 4-[(7-methoxy-2,3-dihydro-1,4-benzothiazepin-4 (5H)yl)methyl]benzoic acid hemifumarate Form 2.

In some embodiments, if an X-ray diffraction pattern of the crystalline form is obtained using the above measurement conditions, then X-ray diffraction peaks substantially as shown in FIG. 6 are observed.

In some embodiments, the X-ray diffraction (XRD) pattern comprises at least two diffraction peaks selected from 7.3±0.1, 13.2±0.1, 14.6±0.1, 17.1±0.1, 18.0±0.1, 18.3±0.1, 23.2±0.1, 23.9±0.1, 24.4±0.1, and 28.6±0.1 degrees two theta (°θ). In some embodiments, the X-ray diffraction (XRD) pattern comprises at least three diffraction peaks selected from 7.3±0.1, 13.2±0.1, 14.6±0.1, 17.1±0.1, 18.0±0.1, 18.3±0.1, 23.2±0.1, 23.9±0.1, 24.4±0.1, and 28.6±0.1 degrees two theta (°θ). In some embodiments, the X-ray diffraction (XRD) pattern comprises at least four diffraction peaks selected from 7.3±0.1, 13.2±0.1, 14.6±0.1, 17.1±0.1, 18.0±0.1, 18.3±0.1, 23.2±0.1, 23.9±0.1, 24.4±0.1, and 28.6±0.1 degrees two theta (°θ). In some embodiments, the X-ray diffraction (XRD) pattern comprises at least five diffraction peaks selected from 7.3±0.1, 13.2±0.1, 14.6±0.1, 17.1±0.1, 18.0±0.1, 18.3±0.1, 23.2±0.1, 23.9±0.1, 24.4±0.1, and 28.6±0.1 degrees two theta (°θ). In some embodiments, the X-ray diffraction pattern comprises a peak at 7.3±0.1 degrees two theta (°θ).

In some embodiments, the crystalline form is characterized by an X-ray diffraction (XRD) pattern comprising diffraction peaks at 7.3±0.1, 14.6±0.1, 18.0±0.1, 22.4±0.1, and 24.4±0.1 degrees two theta (°θ).

In some embodiments, the crystalline form is characterized by an X-ray diffraction (XRD) pattern comprising diffraction peaks at 7.3±0.1, 11.1±0.1, 14.6±0.1, 18.0±0.1, 19.2±0.1, 22.4±0.1, 23.2±0.1, and 24.4±0.1 degrees two theta (°θ).

In some embodiments, the crystalline form is characterized by an X-ray diffraction (XRD) pattern comprising diffraction peaks at 7.3±0.1, 11.0±0.1, 11.1±0.1, 11.5±0.1, 13.2±0.1, 14.6±0.1, 15.2±0.1, 17.1±0.1, 18.0±0.1, 18.3±0.1, 19.2±0.1, 20.2±0.1, 21.4±0.1, 22.4±0.1, 23.2±0.1, 23.9±0.1, 24.4±0.1 and 28.6±0.1 degrees two theta (°θ).

In some embodiments, the crystalline form is characterized by an X-ray diffraction (XRD) pattern substantially as shown in FIG. 6. Form 2 is characterized by an X-ray diffraction (XRD) pattern substantially as shown in TABLE 2.

TABLE 2

XRD peaks of Form 2

| No. | 2-Theta [° 2θ] | Relative Intensity (%) |
|---|---|---|
| 1 | 7.3 | 39.1 |
| 2 | 11.0 | 19.9 |

TABLE 2-continued

XRD peaks of Form 2

| No. | 2-Theta [° 2θ] | Relative Intensity (%) |
|---|---|---|
| 3 | 11.1 | 32.6 |
| 4 | 11.5 | 29.9 |
| 5 | 13.2 | 23.7 |
| 6 | 14.6 | 99.3 |
| 7 | 15.2 | 20.1 |
| 8 | 17.1 | 24.6 |
| 9 | 18.0 | 100.0 |
| 10 | 18.3 | 24.6 |
| 11 | 19.2 | 36.4 |
| 12 | 20.2 | 24.2 |
| 13 | 21.4 | 24.0 |
| 14 | 22.4 | 69.6 |
| 15 | 23.2 | 38.0 |
| 16 | 23.9 | 24.5 |
| 17 | 24.4 | 72.9 |
| 18 | 28.6 | 45.6 |

In some embodiments, provided herein is a composition comprising a crystalline form of 4-[(7-methoxy-2,3-dihydro-1,4-benzothiazepin-4(5H)yl)methyl]benzoic acid hemifumarate, wherein if a melting point of the crystalline form is obtained by (a) equilibrating a sample of said crystalline form at a temperature of about 20° C. in a temperature-controlled chamber; and (b) increasing the temperature of the temperature-controlled chamber at about 10° C./minute to 250° C. using a differential scanning calorimetry instrument, then a melting point of 208-210° C. ($T_{onset}$) is obtained. The differential scanning calorimetry instrument can be, for example, DSC Q1000 or DSC Q2000.

Figure 7:
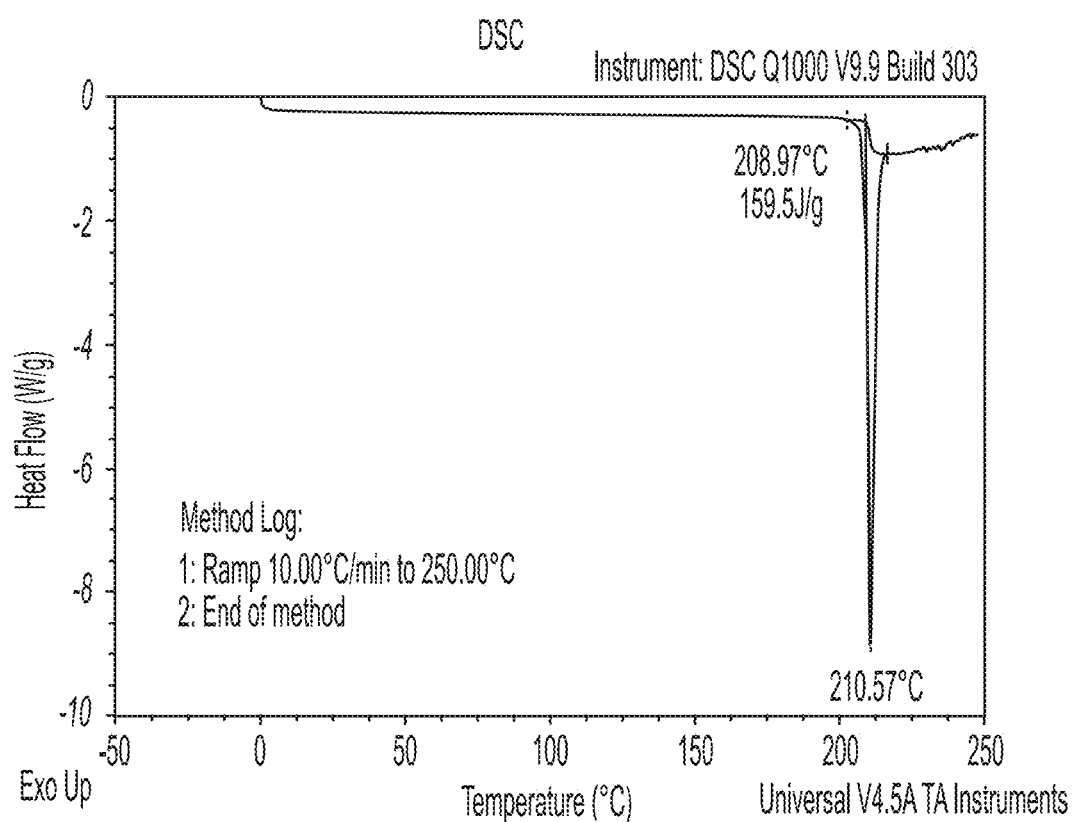
FIG. 7 depicts a characteristic Differential Scanning calorimetry (DSC) profile of 4-[(7-methoxy-2,3-dihydro-1,4-benzothiazepin-4(5H)yl)methyl]benzoic acid hemifumarate Form 2.

In some embodiments, provided herein is a composition comprising a crystalline form of 4-[(7-methoxy-2,3-dihydro-1,4-benzothiazepin-4(5H)yl)methyl]benzoic acid hemifumarate, wherein the crystalline form is characterized by a differential scanning calorimetry (DSC) profile substantially as shown in FIG. 7. In some embodiments, the crystalline form is further characterized by melting point at about 208-210° C. ($T_{onset}$). As shown in FIG. 7, an illustrative sample of the crystalline form has a $T_{onset}$: 209.5° C., $T_{peak}$: 210.7° C. (melting/degradation).

Figure 8:
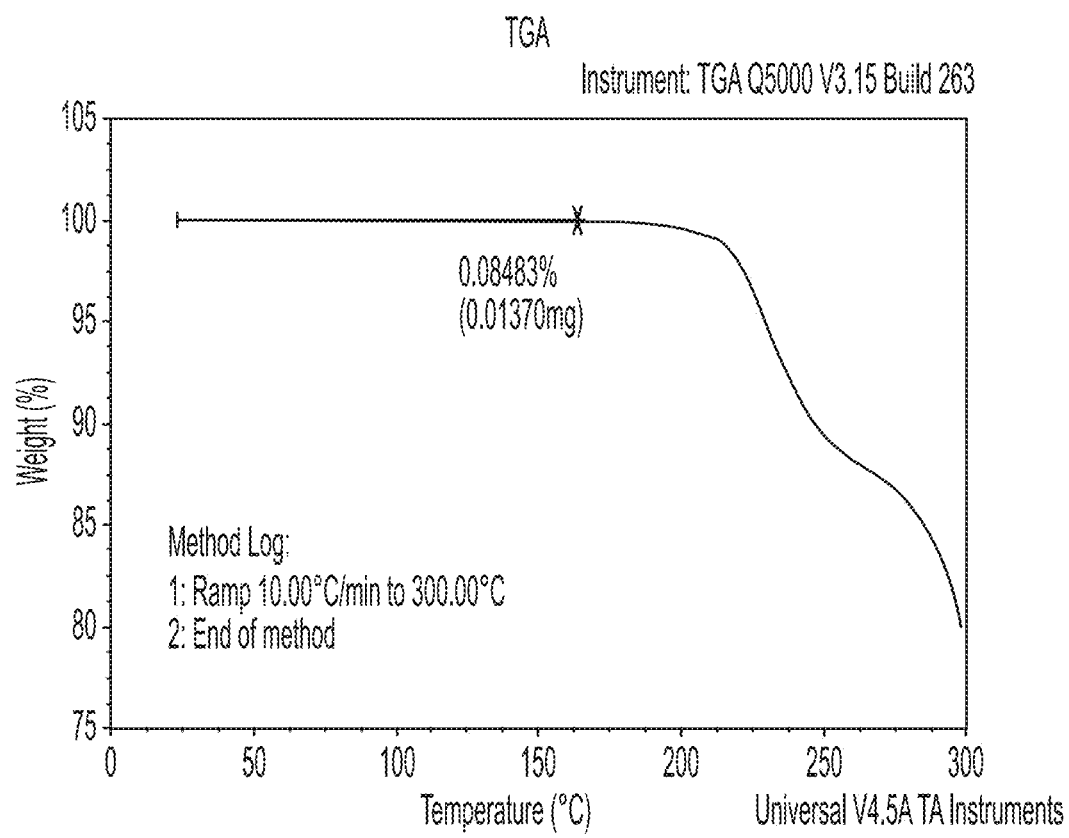
FIG. 8 depicts a characteristic Thermogravimetric analysis (TGA) profile 4-[(7-methoxy-2,3-dihydro-1,4-benzothiazepin-4(5H)yl)methyl]benzoic acid hemifumarate Form 2.

In some embodiments, the crystalline form is further characterized by a thermo gravimetric analysis (TGA) profile. In some embodiments, provided herein is a composition comprising a crystalline 4-[(7-methoxy-2,3-dihydro-1,4-benzothiazepin-4(5H)yl)methyl]benzoic acid, hemifumarate, wherein, if a thermogravimetric analysis of the crystalline form is obtained by: (a) equilibrating a sample of said crystalline form at 25° C. in a temperature-controlled chamber; and (b) increasing the temperature at a scan rate of about 10° C./minute to 250° C. using a thermogravimetric analysis instrument, then a thermogravimetric analysis profile substantially as shown in FIG. 8 is obtained. In some embodiments, the loss of mass before melting degradation is about <0.1%. In some embodiments, the crystalline form is not hygroscopic. The thermogravimetric analysis instrument can be, for example, TGAQ5000.

In some embodiments, provided herein is a composition comprising a crystalline 4-[(7-methoxy-2,3-dihydro-1,4-benzothiazepin-4(5H)yl)methyl]benzoic acid, hemifumarate, wherein the crystalline form is characterized by a thermogravimetric analysis profile substantially as shown in FIG. 8.

In some embodiments, the crystalline form is further characterized by a dynamic vapor sorption (DVS) profile. In some embodiments, provided herein is a composition comprising a crystalline 4-[(7-methoxy-2,3-dihydro-1,4-benzothiazepin-4(5H)yl)methyl]benzoic acid, hemifumarate, wherein if a dynamic vapor sorption profile of the crystalline form is obtained by: (a) equilibrating a sample of said crystalline form at 25° C. and 50% relative humidity in a temperature-controlled and humidity controlled chamber until mass variation is less than 0.002% per minute for 6 hours; (b) increasing the relative humidity from 50% to 90% at a rate of 10% per hour; (c) equilibrating the sample at 90% relative humidity until mass variation of less than 0.002% per minute for 6 hours is observed; (d) decreasing the relative humidity from 90% to 0% at a rate of 10% per hour; (e) equilibrating the sample at 0% relative humidity until mass variation of less than 0.002% per minute for 6 hours is observed; and (f) increasing the relative humidity from 0% to 50% at a rate of 10% per hour, then a dynamic vapor sorption profile substantially as shown in FIG. 9 is obtained.

Figure 9:
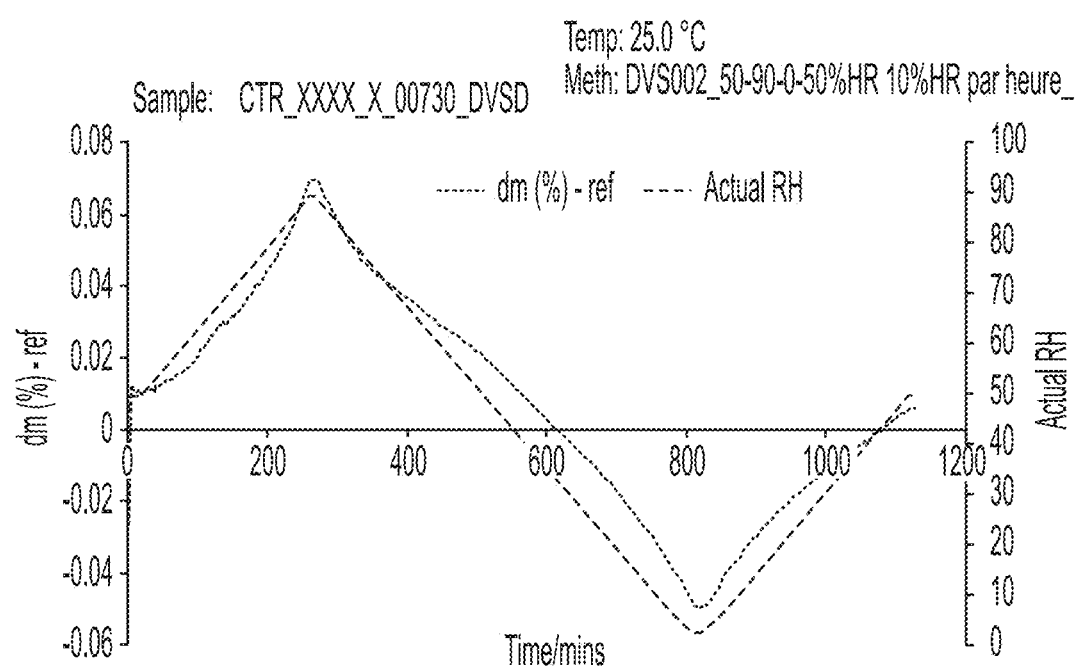
FIG. 9 depicts a characteristic Dynamic Vapor Sorption (DVS) profile of 4-[(7-methoxy-2,3-dihydro-1,4-benzothiazepin-4(5H)yl)methyl]benzoic acid hemifumarate Form 2.

In some embodiments, provided herein is a composition comprising a crystalline 4-[(7-methoxy-2,3-dihydro-1,4-benzothiazepin-4(5H)yl)methyl]benzoic acid, hemifumarate, wherein the crystalline form is characterized by a dynamic vapor sorption profile substantially as shown in FIG. 9.

In some embodiments, the a crystalline 4-[(7-methoxy-2,3-dihydro-1,4-benzothiazepin-4(5H)yl)methyl]benzoic acid, hemifumarate, is anhydrous. In some embodiments, the a crystalline 4-[(7-methoxy-2,3-dihydro-1,4-benzothiazepin-4(5H)yl)methyl]benzoic acid hemifumarate is substantially anhydrous.

Comparison of Form 1 and Form 2

Forms 1 and 2 can be differentiated, for example, by an overlay of the XRD analysis as depicted in FIG. 11. Top: Form 1. Bottom: Form 2. Form 1 comprises unique peaks at least at 9.8±0.1, 11.8±0.1, 13.5±0.1, 14.0±0.1, 14.3±0.1, 17.4±0.1, 18.9±0.1, 19.6±0.1, 22.1±0.1, 26.6±0.1, and 27.2±0.1 degrees two theta (°θ). Form 2 comprises unique peaks at least at 7.3±0.1, 13.2±0.1, 14.6±0.1, 17.1±0.1, 18.0±0.1, 18.3±0.1, 23.2±0.1, 23.9±0.1, 24.4±0.1, and/or 28.6±0.1 degrees two theta (°θ).

Methods of Preparation

The present disclosure further processes methods for preparing the polymorphs described herein.

In some embodiments, the present disclosure provides a process for synthesis of a crystalline form of 4-[(7-methoxy-2,3-dihydro-1,4-benzothiazepin-4(5H)yl)methyl]benzoic acid hemifumarate, the process comprising: a. reacting 4-[(7-methoxy-2,3-dihydro-1,4-benzothiazepin-4(5H)yl)methyl]benzoic acid or an ionized form thereof with fumaric acid in presence of isopropanol to generate a reaction mixture, the reaction mixture comprising a precipitate; b. isolating the precipitate from a.; c. washing the precipitate from b. with isopropanol; and d. drying the precipitate from c. to obtain particles, the particles comprising the crystalline form of 4-[(7-methoxy-2,3-dihydro-1,4-benzothiazepin-4 (5H)yl)methyl]benzoic acid hemifumarate, wherein if a melting point of the crystalline form is obtained by: (a) equilibrating a sample of said crystalline form at a temperature of about 20° C. in a temperature-controlled chamber; and (b) increasing the temperature of the temperature-controlled chamber at a scan rate of about 10° C./minute to 250° C. using a differential scanning calorimetry instrument, then a melting point of 201-203° C. ($T_{onset}$) is obtained.

In some embodiments, the present disclosure provides a process for synthesis of a crystalline form of 4-[(7-methoxy-2,3-dihydro-1,4-benzothiazepin-4(5H)yl)methyl]benzoic acid hemifumarate, the process comprising: a. reacting 4-[(7-methoxy-2,3-dihydro-1,4-benzothiazepin-4(5H)yl)

methyl]benzoic acid or an ionized form thereof with fumaric acid in presence of isopropanol to generate a reaction mixture, the reaction mixture comprising a precipitate; b. isolating the precipitate from a.; c. washing the precipitate from b. with isopropanol; and d. drying the precipitate from c. to obtain particles, the particles comprising the crystalline form of 4-[(7-methoxy-2,3-dihydro-1,4-benzothiazepin-4 (5H)yl)methyl]benzoic acid hemifumarate.

In some embodiments, the present disclosure provides a process for synthesis of a crystalline form of 4-[(7-methoxy-2,3-dihydro-1,4-benzothiazepin-4(5H)yl)methyl]benzoic acid hemifumarate, the process comprising: a. reacting 4-[(7-methoxy-2,3-dihydro-1,4-benzothiazepin-4(5H)yl) methyl]benzoic acid or an ionized form thereof with fumaric acid in presence of a mixture of dimethyl sulfoxide (DMSO) and water to generate a reaction mixture, the reaction mixture comprising a precipitate; b. isolating the precipitate from a.; c. washing the precipitate from b. with water and acetone; and d. drying the precipitate from c. to obtain particles, the particles comprising the crystalline form of 4-[(7-methoxy-2,3-dihydro-1,4-benzothiazepin-4(5H)yl) methyl]benzoic acid hemifumarate, wherein if a melting point of the crystalline form is obtained by (a) equilibrating a sample of said crystalline form at a temperature of about 20° C. in a temperature-controlled chamber; and (b) increasing the temperature of the temperature-controlled chamber at a scan rate of about 10° C./minute to 250° C., using a differential scanning calorimetry instrument, then a melting point of 208-210° C. ($T_{onset}$) is obtained.

In some embodiments, the present disclosure provides a process for synthesis of a crystalline form of 4-[(7-methoxy-2,3-dihydro-1,4-benzothiazepin-4(5H)yl)methyl]benzoic acid hemifumarate, the process comprising: a. reacting 4-[(7-methoxy-2,3-dihydro-1,4-benzothiazepin-4(5H)yl) methyl]benzoic acid or an ionized form thereof with fumaric acid in presence of a mixture of dimethyl sulfoxide (DMSO) and water to generate a reaction mixture, the reaction mixture comprising a precipitate; b. isolating the precipitate from a.; c. washing the precipitate from b. with water and acetone; and d. drying the precipitate from c. to obtain particles, the particles comprising the crystalline form of 4-[(7-methoxy-2,3-dihydro-1,4-benzothiazepin-4(5H)yl) methyl]benzoic acid hemifumarate.

In some embodiments, the process further comprises (i) cooling the reaction mixture generated in a., when (i) is performed prior to b. Cooling the reaction mixture comprises, e.g., reducing the reaction temperature from about room temperate (about 25° C.) to less than about 15° C., or less than about 15° C. or less than about 5° C., for example.

Particle Size

In some embodiments, the size of a particle or mean particle size of a population of particles can be reduced to a suitable value. The crystalline forms of 4-[(7-methoxy-2,3-dihydro-1,4-benzothiazepin-4(5H)yl)methyl]benzoic acid, hemifumarate, Form 1 and Form 2, can be provided in a micronized or non-micronized form. A formulation can be prepared to have a desired property such as particle sizes in a desired range or a desired mean particle size. A population of particles can have a particle size distribution in which a portion of the particles each have a longest diameter that is shorter than a given value. The portion can be, for example, 90% by mass ($D_{90}$), 50% by mass ($D_{50}$), or 10% by mass ($D_{10}$).

For example, the particle size can be reduced by milling or grinding, or any other process that reduces particle size. Impact milling such as pin milling provides higher blend uniformity to the final composition relative to other types of milling. Cooling of the material being milled, for example, using liquid nitrogen, during milling avoids heating the compound to undesirable temperatures. The D particle size during this milling step can be reduced to, for example, no greater than about 100 µm or no greater than about 50 µm. For example, milled forms can be reduced to a $D_{90}$ particle size of no greater than about 100 µm, no greater than about 95 µm, no greater than about 90 µm, no greater than about 85 µm, no greater than about 80 µm, no greater than about 75 µm, no greater than about 70 µm, no greater than about 65 µm, no greater than about 60 µm, no greater than about 55 µm, or no greater than about 50 µm. For example, milled forms can be reduced to a $D_{90}$ particle size of between about 50 µm and about 100 µm (i.e., 50 µm≤$D_{90}$≤100 µm), between about 50 µm and about 90 µm (i.e., 50 µm≤$D_{90}$≤90 µm), between about 60 µm and about 90 µm (i.e., 60 µm≤$D_{90}$≤90 µm), between about 70 µm and about 90 µm (i.e., 70 µm≤$D_{90}$≤90 µm), or between about 80 µm and about 90 µm (i.e., 80 µm≤$D_{90}$≤90 µm).

Alternatively, milled forms can be reduced to a $D_{50}$ particle size of no greater than about 50 µm, no greater than about 45 µm, no greater than about 40 µm, no greater than about 35 µm, no greater than about 30 µm, no greater than about 25 µm, no greater than about 20 µm, no greater than about 15 µm, or no greater than about 10 µm. For example, milled forms can be reduced to a $D_{50}$ particle size of between about 10 µm and about 50 µm (i.e., 10 µm≤$D_{50}$≤50 µm), between about 10 µm and about 40 µm (i.e., 10 µm≤$D_{50}$≤40 µm), between about 10 µm and about 30 µm (i.e., 10 µm≤$D_{50}$≤30 µm), and between about 10 µm and about 20 µm (i.e., 10 µm≤$D_{50}$≤20 µm).

In some embodiments, the particle size can further be reduced to yield micronized particles having particle size of no greater than about 10 µm or between about 1 and about 10 µm. Such micronized forms can have a $D_{90}$ particle size of no greater than about 10 µm, no greater than about 9 µm, no greater than about 8 µm, no greater than about 7 µm, no greater than about 6 µm, no greater than about 5 µm, no greater than about 4 µm, no greater than about 3 µm, no greater than about 2 µm, about 1 µm, or smaller than 1 µm. For example, micronized forms can be reduced to a $D_{90}$ particle size of between about 1 µm and about 10 µm (i.e., 1 µm≤$D_{90}$≤10µm), between about 2 µm and about 9 µm (i.e., 2 µm≤$D_{50}$≤9 µm), between about 5 µm and about 9 µm (i.e., 5 µm≤$D_{90}$≤9 µm), or between about 1 µm and about 5 µm (i.e., 1 µm≤$D_{90}$≤5 µm).

Alternatively, micronized forms can be reduced to a $D_{50}$ particle size of up to about 5 µm, up to about 4 µm, up to about 3 µm, up to about 2 µm, about 1 µm, or smaller than 1 µm. For example, micronized forms can be reduced to a $D_{50}$ particle size of between about 1 µm and about 10 µm (i.e., 1 µm≤$D_{50}$≤10 µm), between about 1 µm and about 5 µm (i.e., 1 µm≤$D_{50}$≤5 µm), and between about 1 µm and about 3 µm (i.e., 1 µm≤$D_{50}$≤3 µm).

In some embodiments, the crystalline form comprises a population of particles, wherein at least about 90% by mass of the particles comprise a diameter of no greater than about 20 microns. In some embodiments, the crystalline form comprises a population of particles, wherein at least about 50% by mass of the particles comprise a diameter of no greater than 10 microns. In some embodiments, the crystalline form comprises a population of particles, wherein at least about 50% by mass of the particles comprise a diameter of between about 6.9 microns and about 9.75 microns.

In some embodiments, the crystalline form comprises a population of particles, wherein at least about 90% by mass of the particles comprise a diameter of no greater than about 90 microns. In some embodiments, the crystalline form comprises a population of particles, wherein at least about 50% by mass of the particles comprise a diameter of no greater than about 30 microns. In some embodiments, the crystalline form comprises a population of particles, wherein at least about 50% by mass of the particles comprise a diameter of between about 10 microns and about 30 microns.

Therapeutic Use

The present disclosure provides crystalline polymorphic forms of 4-[(7-methoxy-2,3-dihydro-1,4-benzothiazepin-4(5H)yl)methyl]benzoic acid hemifumarate, Form 1 and Form 2, that are capable, for example, of treating conditions, disorders, and diseases associated with Ryanodine Receptors (RyRs).

In some embodiments, the present disclosure provides compounds that are RyR modulators, for example, a Rycal compound. Rycal compounds are small molecules that can, for example, bind to leaky RyR subunits, restore Calstabin binding, and repair the channel leak. In some embodiments, Rycals bind to leaky RyR channels, restore Calstabin binding, and fix the channel leak without blocking the RyR channel. In some embodiments, Rycal compounds are capable of fixing a leak in RyR channels, for example, RyR1, RyR2, and/or RyR3 channels. In some embodiments, the crystalline forms of the disclosure enhance association and/or inhibit dissociation of RyR and Calstabin (e.g., RyR1 and Calstabin1; RyR2 and Calstabin2; and RyR3 and Calstabin1).

Non-limiting examples of conditions, disorders, and diseases associated with RyRs include disorders and diseases that can be treated and/or prevented by modulating RyRs and include, for example, a cardiac disorder or disease, a musculoskeletal disorder or disease, cancer associated muscle weakness, malignant hyperthermia, and diabetes. A compound herein can also lessen the likelihood of the occurrence of such a condition.

Non-limiting examples of routes of administration of the compounds herein include oral routes, intraduodenal routes, parenteral injection (including intravenous, subcutaneous, intraperitoneal, intramuscular, intravascular, and infusion), topical, and rectal administration. In some embodiments, the compounds and compositions described herein are administered orally.

In some embodiments, the present disclosure provides a method of treating or preventing a condition by administering to a subject in need thereof a therapeutically-effective amount of a composition, the composition comprising crystalline form of 4-[(7-methoxy-2,3-dihydro-1,4-benzothiazepin-4(5H)yl)methyl]benzoic acid hemifumarate, Form 1, or a pharmaceutical composition in unit dosage form comprising such compound.

In some embodiments, the present disclosure provides a method of treating or preventing a condition by administering to a subject in need thereof a therapeutically-effective amount of a composition, the composition comprising crystalline form of 4-[(7-methoxy-2,3-dihydro-1,4-benzothiazepin-4(5H)yl)methyl]benzoic acid hemifumarate, Form 2, or a pharmaceutical composition in unit dosage form comprising such compound.

In some embodiments, the present disclosure provides a therapeutically-effective amount of a crystalline form of 4-[(7-methoxy-2,3-dihydro-1,4-benzothiazepin-4(5H)yl)methyl]benzoic acid hemifumarate, Form 1, or a pharmaceutical composition in unit dosage form comprising such compound, for use in a method of treating or preventing a condition.

In some embodiments, the present disclosure provides a therapeutically-effective amount of a crystalline form of 4-[(7-methoxy-2,3-dihydro-1,4-benzothiazepin-4(5H)yl)methyl]benzoic acid hemifumarate, Form 2, or a pharmaceutical composition in unit dosage form comprising such compound, for use in a method of treating or preventing a condition.

In some embodiments, the present disclosure relates to a use of a crystalline form of 4-[(7-methoxy-2,3-dihydro-1,4-benzothiazepin-4(5H)yl)methyl]benzoic acid hemifumarate, Form 1, or a pharmaceutical composition in unit dosage form comprising such compound, for the manufacture of a medicament.

In some embodiments, the present disclosure relates to a use of a crystalline form of 4-[(7-methoxy-2,3-dihydro-1,4-benzothiazepin-4(5H)yl)methyl]benzoic acid hemifumarate, Form 2, or a pharmaceutical composition in unit dosage form comprising such compound, for the manufacture of a medicament.

In some embodiments, the condition, disorder, or disease is associated with an abnormal function of RyR1. In some embodiments, the condition, disorder, or disease is associated with an abnormal function of RyR2. In some embodiments, the condition, disorder or disease is associated with an abnormal function of RyR3.

In some embodiments, the condition is a cardiac disorder or disease. In some embodiments, the condition is a musculoskeletal disorder or disease. In some embodiments, the condition is cancer associated muscle weakness. In some embodiments, the condition is malignant hyperthermia. In some embodiments, the condition is diabetes.

Ryanodine Receptors: Excitation-Contraction Coupling (ECC) Process

The sarcoplasmic reticulum (SR) is a structure in cells that functions, among other things, as a specialized intracellular calcium ($Ca^{2+}$) store. Ryanodine receptors (RyRs) are channels in the SR, which open and close to regulate the release of $Ca^{2+}$ from the SR into the intracellular cytoplasm of the cell. Release of $Ca^{2+}$ into the cytoplasm from the SR increases cytoplasmic $Ca^{2+}$ concentration. Open probability of RyRs refers to the likelihood that a RyR is open at any given moment, and therefore capable of releasing $Ca^{2+}$ into the cytoplasm from the SR.

The RyR is the major $Ca^{2+}$ release channel on the SR responsible for excitation-contraction coupling (ECC) in striated muscle. Among the 3 known RyR isoforms (RyR1, RyR2 and RyR3), RyR1 is widely expressed and is the predominant isoform expressed in mammalian skeletal muscle, whereas RyR2 is also widely expressed and is the predominant form found in cardiac muscle. RyR3 expression is low in adult skeletal muscle. RyR subtypes exhibit a high degree of structural and functional homology. The subtypes form a large sarcoplasmic membrane complex, consisting of four monomers that constitute a $Ca^{2+}$ release channel associated with proteins, such as kinases, phosphatases, phosphodiesterases, and other regulatory subunits.

$Ca^{2+}$ release from the SR is modulated by several RyR binding proteins. Calmodulin, a key mediator of $Ca^{2+}$ signaling, exerts both positive and negative effects on RyR open probability. Calstabin1 (FKBP12) and calstabin2 (FKBP12.6) stabilize the closed state of RyR1 and RyR2, respectively. Calstabin1 associates predominantly with skeletal muscle RyR1, while cardiac muscle RyR2 has the highest affinity for Calstabin2.

Mutations in RYR1 or RYR2 can cause decreased binding of Calstabin1 and Calstabin 2, respectively. Stress-induced post-translational modifications of RyRs including PKA phosphorylation, oxidation, and nitrosylation also can cause decreased binding of Calstabins to RyR channels. Genetic mutations and/or stress-induced posttranslational modifications of the channel can result in dissociation of Calstabin from RyRs and cause the channels to become leaky channels. The dissociation of Calstabin can lead to leaky channels, which exhibit a pathologic increase in the open probability under resting conditions. The SR $Ca^{2+}$ leak leads to a reduction in SR $Ca^{2+}$ content, with less $Ca^{2+}$ available for release and consequently weaker muscle contractions. The intracellular calcium leak has distinct pathological consequences depending on which tissue is involved.

Ryanodine Receptor 2 and Cardiac Diseases

In some embodiments, the RyR-associated condition is a cardiac disorder or disease that implicates the Ryanodine Receptor 2 (RyR2). The RyR2 channel plays a major role in intracellular calcium handling by regulating the release of $Ca^{2+}$ from the sarcoplasmic reticulum (SR) in cardiac myocytes required for ECC in cardiac muscle. The RyR2 channel is a macromolecular complex that includes four identical RyR2 subunits, each of which binds one Calstabin2 (FKBP12.6), and other interacting proteins such as phosphatases and kinases. Binding of Calstabin2 stabilizes the channel in the closed state during the resting phase of the heart (diastole), thereby preventing diastolic calcium leak from the SR, and functionally couples groups of RyR2 channels to allow synchronous opening during excitation-contraction coupling.

Phosphorylation of RyR2 by protein kinase A (PKA) is an important part of the fight-or-flight response. Phosphorylation increases cardiac EC coupling gain by augmenting the amount of $Ca^{2+}$ released for a given trigger. The process strengthens muscle contraction and improves exercise capacity. This signaling pathway provides a mechanism by which activation of the sympathetic nervous system (SNS), in response to stress, results in increased cardiac output. Phosphorylation of RyR2 by PKA increases the sensitivity of the channel to calcium-dependent activation. The increased sensitivity leads to increased open probability and increased calcium release from the SR into the intracellular cytoplasm.

Heart failure (HF) is characterized by a sustained hyperadrenergic state in which serum catecholamine levels are chronically elevated. One consequence of this chronic hyperadrenergic state is persistent PKA hyperphosphorylation of RyR2, such that 3-4 out of the four Ser2808 in each homotetrameric RyR2 channel are chronically phosphorylated. Chronic PKA hyperphosphorylation of RyR2 is associated with depletion of the channel-stabilization subunit Calstabin2 from the RyR2 channel macromolecular complex. Depletion of Calstabin2 results in a diastolic SR $Ca^{2+}$ leak from the RyR complex, and contributes to impaired contractility. Due to the activation of inward depolarizing currents, this diastolic SR $Ca^{2+}$ leak also is associated with fatal cardiac arrhythmias. Indeed, mice engineered with RyR2 lacking the PKA phosphorylation site (RyR-S2808A) are protected from HF progression after myocardial infarction (MI). In addition, chronic PKA hyperphosphorylation of RyR2 in HF is associated with remodeling of the RyR2 macromolecular complex. The remodeling includes depletion of phosphatases PP1 and PP2a (impairing dephosphorylation of Ser2808) and the cAMP-specific type 4 phosphodiesterase (PDE4D3) from the RyR2 complex. Depletion of PDE4D3 from the RyR2 complex causes sustained elevation of local cAMP levels. Thus, diastolic SR $Ca^{2+}$ leak contributes to HF progression and arrhythmias. Additional post-translational modifications of the RyR channel (oxidation and nitrosylation) further drive the leak.

RyR leak is associated with a variety of cardiac disorders, conditions, and diseases. In some embodiments, the cardiac disorder or disease is heart failure. In some embodiments, the cardiac disorder or disease is myocardial infarction (MI). In some embodiments, the heart failure is congestive heart failure. In some embodiments, the heart failure is chronic heart failure. In some embodiments, the heart failure is systolic heart failure. In some embodiments, the heart failure is diastolic heart failure. In some embodiments, the heart failure is acute decompensated heart failure. In some embodiments, the heart failure is heart failure with reduced or preserved ejection fraction. In some embodiments, the heart failure is acute heart failure, for example, for preservation of cardiac function post myocardial infarction or cardiomyopathy.

In some embodiments, the cardiac disorder or disease comprises cardiac ischemia/reperfusion (FR) injury. FR injury can occur following coronary angioplasty or following thrombolysis for the treatment of myocardial infarction (MI) or during/following cardiac bypass surgery or heart transplant.

In some embodiments, the cardiac disorder or disease is characterized by an irregular heartbeat or an arrhythmia. In some embodiments, the cardiac disorder or disease is catecholaminergic polymorphic ventricular tachycardia (CPVT). In some embodiments, the cardiac disorder or disease is, or is characterized by, an atrial arrhythmia. In some embodiments, the cardiac disorder or disease is, or is characterized by, a ventricular arrhythmia. In some embodiments, the cardiac disorder or disease is, or is characterized by, atrial fibrillation. In some embodiments, the cardiac disorder or disease is, or is characterized by, ventricular fibrillation. In some embodiments, the cardiac disorder or disease is, or is characterized by, atrial tachyarrhythmia. In some embodiments, the cardiac disorder or disease is, or is characterized by, ventricular tachyarrhythmia. In some embodiments, the cardiac disorder or disease is, or is characterized by, atrial tachycardia. In some embodiments, the cardiac disorder or disease is, or is characterized by, ventricular tachycardia. In some embodiments, the cardiac disorder or disease is, or is characterized by, sick sinus syndrome. In some embodiments, the cardiac disorder or disease is, or is characterized by, Sudden infant death syndrome (SIDS). In some embodiments, the cardiac disorder or disease is, or is characterized by, sudden unexplained death (SUD).

In some embodiments, the cardiac disorder or disease is Catecholaminergic Polymorphic Ventricular Tachycardia (CPVT). CPVT is one of the most lethal inherited arrhythmogenic disorders. CPVT occurs in the absence of structural heart disease and is characterized by adrenergically mediated ventricular arrhythmias associated with a high incidence of Sudden Cardiac Death (SCD). Patients usually present in the first or second decade of life with stress-induced syncope. CPVT is associated with mutations in two genes that code for proteins associated with the sarcoplasmic reticulum (SR) of the cardiomyocyte. The most frequently observed Form 1s CPVT type 1, an autosomal dominant form due to mutations in RyR2. This type encodes an intracellular SR calcium release channel. CPVT-associated RyR2 mutations result in leaky RyR2 channels due to the decreased binding of the Calstabin-2 (FKBP12.6) subunit, which stabilizes the closed state of the channel. Mice heterozygous for the R2474S mutation (which occurs in humans with CPVT1) in RyR2 (RyR2-R2474S mice) can exhibit exercise-induced ventricular arrhythmias and sudden cardiac death. Treatment with Rycals that enhance the binding of Calstabin2 to the mutant RyR2-R2474S channel can inhibit the channel leak and prevent cardiac arrhythmias.

Ryanodine Receptor 1 and Musculoskeletal Diseases

In some embodiments, the RyR-associated condition is a musculoskeletal disorder or disease that implicates the Ryanodine Receptor 1 (RyR1). The RyR1 macromolecular complex consists of a tetramer of the 560-kDa RyR1 subunit that forms a scaffold for proteins that regulate channel function including PKA and the phosphodiesterase 4D3 (PDE4D3), protein phosphatase 1 (PP1) and Calstabin1. A-kinase anchor protein (mAKAP) targets PKA and PDE4D3 to RyR1, whereas spinophilin targets PP1 to the channel. The catalytic and regulatory subunits of PKA, PP1, and PDE4D3 regulate PKA-mediated phosphorylation of RyR1 at Ser2843 (Ser2844 in the mouse). PKA-mediated phosphorylation of RyR1 at Ser2844 increases the sensitivity of the channel to cytoplasmic $Ca^{2+}$, reduces the binding affinity of Calstabin1 for RyR1, and destabilizes the closed state of the channel.

Calstabin1 concentrations in skeletal muscle can be approximately 200 nM. PKA phosphorylation of RyR1 can reduce the binding affinity of Calstabin1 for RyR1 from approximately 100-200 nM to more than 600 nM. Thus, under physiologic conditions, reduction in the binding affinity of Calstabin1 for RyR1, resulting from PKA phosphorylation of RyR1 at Ser2843, is sufficient to reduce substantially the amount of Calstabin1 present in the RyR1 complex. Chronic PKA hyperphosphorylation of RyR1 at Ser2843) results in leaky channels (i.e., channels prone to opening at rest), which contribute to the skeletal muscle dysfunction that is associated with persistent hyperadrenergic states such as those in individuals with heart failure.

Moreover, regulation of RyR1 by posttranslational modifications other than phosphorylation, such as by nitrosylation of free sulfhydryl groups on cysteine residues (S-nitrosylation), and channel oxidation, can increase RyR1 channel activity. S-nitrosylation and oxidation of RyR1 each can reduce Calstabin1 binding to RyR1.

In some embodiments, the musculoskeletal disorder or disease is a congenital myopathy or congenital muscular dystrophy (CMD). Congenital muscular dystrophy is present at birth. CMD is classified based on genetic mutations: 1) genes encoding for structural proteins of the basal membrane or extracellular matrix of the skeletal muscle fibers; 2) genes encoding for putative or demonstrated glycosyltransferases, that in turn affect the glycosylation of dystroglycan, an external membrane protein of the basal membrane; and 3) other. Non-limiting examples of CMD include RYR1-related myopathies (RYR1-RM), Laminin-α2-deficient CMD (MDC1A), Ullrich CMG (UCMDs 1, 2 and 3), Walker-Warburg syndrome (WWS), Muscle-eye-brain disease (MEB), Fukuyama CMD (FCMD), CMD plus secondary laminin deficiency 1 (MDC1B), CMD plus secondary laminin deficiency 2 (MDC1C), CMD with mental retardation and pachygyria (MDC1D), and Rigid spine with muscular dystrophy Type 1 (RSMD1).

In some embodiments, the musculoskeletal disease is RYR1-related congenital myopathy (RYR1-RM). RYR1-RM comprise a group of rare neuromuscular diseases. Affected individuals generally present with delayed motor milestones, muscle weakness, impaired ambulation, and, in severe cases, scoliosis, ophthalmoplegia, and respiratory distress all due to skeletal muscle weakness. Causative variants in RYR1, which encodes the major calcium ($Ca^{2+}$) release channel in skeletal muscle, exert different effects on the RyR1 channel. The variants generally disrupt the normal $Ca^{2+}$ flow between the sarcoplasmic reticulum (SR) and muscle cell cytosol and commonly result in excessive $Ca^{2+}$ leak into the cytosol. Persistent $Ca^{2+}$ leak decreases SR $Ca^{2+}$ that is necessary for ECC. Additionally, chronic SR $Ca^{2+}$ leak results in mitochondrial calcium overload, which impairs mitochondrial function manifested as oxidative overload and reduced ATP production. SR $Ca^{2+}$ leak can also activate the calcium-activated protease calpain, which can cause cellular injury. The oxidative stress, in turn, can further contribute to RyR1 $Ca^{2+}$ leak by channel oxidation and nitrosylation.

In some embodiments, the musculoskeletal disorder or disease is muscular dystrophy. Non-limiting examples of muscular dystrophy include Duchenne Muscular Dystrophy (DMD), Becker's Muscular Dystrophy (BMD), Limb-Girdle Muscular Dystrophy (LGMD), facioscapulohumeral dystrophy, myotonic muscular dystrophy, congenital muscular dystrophy (CMD), distal muscular dystrophy, Emery-Dreifuss muscular dystrophy, and oculopharyngeal muscular dystrophy.

Duchenne muscular dystrophy (DMD) is one of the leading lethal childhood genetic diseases. Mutations in dystrophin associated with DMD lead to a complete loss of the dystrophin protein, thereby disrupting the link between the subsarcolemma cytoskeleton and the extracellular matrix. This link is essential for protecting and stabilizing the muscle against contraction induced injury. Sarcolemmal instability due to mutations in dystrophin has a cascade effect. One major effect is increased cytosolic $Ca^{2+}$ concentration, which leads to activation of $Ca^{2+}$ dependent proteases (calpains). Another effect is inflammation and elevated iNOS activity, which can cause oxidation/nitrosylation of proteins, lipids, and DNA. DMD muscle pathology is progressive and far exceeds the instability of the sarcolemma. Thus the pathology is consistent with the instability of the sarcolemma increasing the susceptibility to further injury. Excessive oxidation or nitrosylation of RyR1 can disrupt the interaction of Calstabin1 with the RyR1 complex, leading to RyR1 leakiness and muscle weakness. Treatment with Rycals improves indices of muscle function.

In some embodiments, the musculoskeletal disorder or disease is cancer cachexia, i.e., cancer associated muscle weakness. In some embodiments, the cancer associated muscle weakness is cancer cachexia, for example, due to a cancer having bone metastases. Muscle weakness and muscle atrophy (cachexia) are common paraneoplastic conditions in cancer patients. These conditions cause significant fatigue and dramatically reduce patients' quality of life. In certain cancers, e.g., prostate and breast cancer with bone metastases, RyR1 is oxidized and induced to become leaky. Repairing the leak by administration of Rycal compounds improves muscle function. Non-limiting examples of cancers associated with cachexia that can be treated with a compound herein include breast cancer, prostate cancer, bone cancer, pancreatic cancer, lung cancer, colon cancer, and gastrointestinal cancer. These conditions cause significant fatigue and dramatically reduce patients' quality of life. The present disclosure provides a method for treating, preventing, and reducing a likelihood of developing muscle weakness in a cancer patient, based, for example, on the presence of a modified (e.g., an oxidized state of RyR1), which state induces RyR1 to become leaky. Prevention of the leak by administration of Rycal compounds can improve muscle function.

In some embodiments, the musculoskeletal condition or disease is age-related loss of muscle mass and force (sarcopenia). Sarcopenia contributes to disability and increased mortality. RyR1 from aged mice can be oxidized, cysteine-nitrosylated, and depleted of Calstabin1, compared to RyR1 from younger (3-6 months) adults. Treating aged mice with Rycals can stabilize the binding of Calstabin1 to RyR1, reduce intracellular calcium leak, decrease reactive oxygen species (ROS), and enhance tetanic $Ca^{2+}$ release, muscle-specific force, and exercise capacity.

In some embodiments, the crystalline polymorphs of the present disclosure are useful in treating Type II diabetes by reducing a likelihood of occurrence of intracellular calcium leak via leaky RyR2. This leak causes mitochondrial calcium overload, and decreased ATP production, which reduces activation of KAP channels. Reduced activation of the channels blocks depolarization of the plasma membrane. This blocking decreases activation of the plasma membrane voltage-gated calcium channel, which is the primary source of calcium required for insulin secretion.

Pharmaceutical Compositions

The polymorphs of the present disclosure can be administered neat or as pharmaceutical compositions for administration to human or animal subjects in a biologically-compatible form suitable for administration in vivo. Subjects can be, for example, elderly adults, adults, adolescents, pre-adolescents, children, toddlers, infants, neonates, and non-human animals. In some embodiments, a subject is a patient.

In some embodiments, the present disclosure provides a pharmaceutical composition form comprising in unit dosage crystalline 4-[(7-methoxy-2,3-dihydro-1,4-benzothiazepin-4(5H)yl)methyl]benzoic acid hemifumarate Form 1, in admixture with a pharmaceutically-acceptable excipient, diluent, and/or carrier. In some embodiments, the present disclosure provides a pharmaceutical composition comprising in unit dosage form crystalline 4-[(7-methoxy-2,3-dihydro-1,4-benzothiazepin-4(5H)yl)methyl]benzoic acid hemifumarate Form 2, in admixture with a pharmaceutically acceptable excipient, diluent, and/or carrier.

Non-limiting examples of routes of administration include oral, sublingual, buccal, parenteral (intravenous, intramuscular or subcutaneous), transdermal, per- or trans-cutaneous, intranasal, intra-vaginal, rectal, ocular, and respiratory (via inhalation administration). Administration can be to the subject's muscles, for example, the subject's cardiac or skeletal muscles. In some embodiments, the compound is administered to the subject by way of targeted delivery to cardiac muscle cells via a catheter inserted into the subject's heart. In some embodiments, the compound is orally administered.

Pharmaceutical compositions for solid oral administration include tablets or dragées, sublingual tablets, gastro-resistant tablets, sachets, capsules including gelatin capsules, powders, and granules. Those for liquid oral, nasal, buccal, or ocular administration include emulsions, solutions, suspensions, drops, syrups, and aerosols. The compounds can also be administered as a suspension or solution via drinking water or with food.

Non-limiting examples of pharmaceutically-acceptable excipients or carriers include organic or inorganic materials that are used as materials for pharmaceutical formulations and are incorporated as any one or more of fillers, diluents, binders, disintegrants, lubricants, glidants, plasticizers, surfactants (wetting agents), buffers (pH adjusting agents), suspending agents, colorants, emulsifiers, flavor-improving agents, gellants, preservatives, solubilizers, stabilizers, sweeteners, tonicity agents, dispersing agents, swelling agents, retardants, absorbents, and/or viscosity-increasing agents.

Non-limiting examples of pharmaceutically-acceptable fillers/diluents include cellulose derivatives including microcrystalline cellulose, silicified microcrystalline cellulose carboxymethyl cellulose, methyl cellulose, hydroxypropyl cellulose, hydroxypropyl methylcellulose, ethyl cellulose, starches, sugars such as mannitol, sucrose, lactose, sorbitol, dextrins (e.g., maltodextrin), and amino-sugars.

Non-limiting examples of pharmaceutically-acceptable binders include microcrystalline cellulose, gum tragacanth, gelatin, polyvinylpyrrolidone, copovidone, hydroxypropyl methylcellulose, and starch.

Non-limiting examples of pharmaceutically-acceptable disintegrants include croscarmellose sodium, sodium carboxymethyl starch, and crospovidone.

Non-limiting examples of pharmaceutically-acceptable lubricants include stearates such as magnesium stearate or zinc stearate, stearic acid, sodium stearyl fumarate, talc, glyceryl behenate, sodium lauryl sulfate, polyethylene glycol, and hydrogenated vegetable oil.

Non-limiting examples of pharmaceutically-acceptable glidants include colloidal silicon dioxide, talc, tribasic calcium phosphate, calcium silicate, cellulose, magnesium silicate, magnesium trisilicate, starch, magnesium stearate, talc, and mineral oil.

Non-limiting examples of moisture barrier agents include stearic acid.

Non-limiting examples of pharmaceutically-acceptable plasticizers include triethyl citrate.

Non-limiting examples of pharmaceutically-acceptable surfactants include sodium laurylsulfate or polysorbates, polyvinyl alcohol (PVA), polyethylene glycols, polyoxyethylene-polyoxypropylene block copolymers known as "poloxamer", polyglycerin fatty acid esters such as decaglyceryl monolaurate and decaglyceryl monomyristate, sorbitan fatty acid ester such as sorbitan monostearate, polyoxyethylene sorbitan fatty acid ester such as polyoxyethylene sorbitan monooleate (Tween), polyethylene glycol fatty acid ester such as polyoxyethylene monostearate, polyoxyethylene alkyl ether such as polyoxyethylene lauryl ether, polyoxyethylene castor oil, and hardened castor oil such as polyoxyethylene hardened castor oil.

Non-limiting examples of pharmaceutically-acceptable flavoring agents include sweeteners such as sucralose and synthetic flavor oils and flavoring aromatics, natural oils, extracts from plants, leaves, flowers, and fruits, and combinations thereof. Non-limiting examples of flavoring agents include cinnamon oils, oil of wintergreen, peppermint oils, clover oil, hay oil, anise oil, eucalyptus, peppermint, vanilla, citrus oil such as lemon oil, orange oil, grape and grapefruit oil, and fruit essences including apple, peach, pear, strawberry, raspberry, cherry, plum, pineapple, and apricot.

Non-limiting examples of pharmaceutically-acceptable pigments or colorants include alumina (dried aluminum hydroxide), annatto extract, calcium carbonate, canthaxanthin, caramel, β-carotene, cochineal extract, carmine, potassium sodium copper chlorophyllin (chlorophyllin-copper complex), dihydroxyacetone, bismuth oxychloride, synthetic iron oxide, ferric ammonium ferrocyanide, ferric ferrocyanide, chromium hydroxide green, chromium oxide greens, guanine, mica-based pearlescent pigments, pyrophyllite, mica, dentifrices, talc, titanium dioxide, aluminum powder, bronze powder, copper powder, and zinc oxide.

Non-limiting examples of buffering or pH adjusting agents include acidic buffering agents such as short chain fatty acids, citric acid, acetic acid, hydrochloric acid, sulfuric acid and fumaric acid; and basic buffering agents such as tris, sodium carbonate, sodium bicarbonate, sodium hydroxide, potassium hydroxide, and magnesium hydroxide.

Non-limiting examples of tonicity enhancing agents include ionic and non-ionic agents such as, alkali metal or alkaline earth metal halides, urea, glycerol, sorbitol, mannitol, propylene glycol, and dextrose.

Non-limiting examples of wetting agents include glycerin, cetyl alcohol, and glycerol monostearate.

Non-limiting examples of preservatives include benzalkonium chloride, benzoxonium chloride, thiomersal, phenylmercuric nitrate, phenylmercuric acetate, phenylmercuric borate, methylparaben, propylparaben, chlorobutanol, benzyl alcohol, phenyl alcohol, chlorohexidine, and polyhexamethylene biguanide.

Non-limiting examples of antioxidants include sorbic acid, ascorbic acid, ascorbate, glycine, α-tocopherol, butylated hydroxyanisole (BHA), and butylated hydroxytoluene (BHT).

In some embodiments, solid dosage forms are coated. In some embodiments, solid dosage forms contain a core, a subcoating layer substantially surrounding the core, and a coating layer substantially surrounding the subcoating layer.

In some embodiments, the subcoating layer comprises a swellable polymer such as a swellable hydrophobic polymer layer (e.g., hydroxypropyl cellulose (HPC) or hydroxypropylmethyl cellulose (HPMC).

In some embodiments, the coating layer comprises an enteric polymer. Non-limiting examples of enteric polymers include hydroxypropyl methylcellulose acetate succinate (hypromellose acetate succinate, HPMC-AS), cellulose acetate phthalate, hydroxypropyl methylcellulose phthalate, cellulose acetate trimellitate, polyvinyl acetate phthalate, methacrylic acid/methacrylic acid ester copolymers (e.g., poly(methacrylic acid-co-methyl methacrylate), methacrylic acid/acrylic acid ester copolymers, shellac (esters of aleurtic acid).

In some embodiments, pharmaceutically-acceptable carriers or excipients are used to formulate liquids, gels, syrups, elixirs, slurries, or suspensions for oral ingestion by a subject. Non-limiting examples of solvents used in an oral dissolvable formulation can include water, ethanol, isopropanol, saline, physiological saline, DMSO, potassium phosphate buffer, phosphate buffer saline (PBS), sodium phosphate buffer, 4-2-hydroxyethyl-1-piperazineethanesulfonic acid buffer (HEPES), 3-(N-morpholino)propanesulfonic acid buffer (MOPS), piperazine-N,N'-bis(2-ethanesulfonic acid) buffer (PIPES), and saline sodium citrate buffer (SSC). Non-limiting examples of co-solvents used in an oral dissolvable formulation can include sucrose, urea, cremaphor, and potassium phosphate buffer.

Pharmaceutical compositions for parenteral injections can include sterile solutions, which can be aqueous or non-aqueous, dispersions, suspensions, emulsions, and also sterile powders for the reconstitution of injectable solutions or dispersions. The polymorphs can be combined with a sterile aqueous solution that is isotonic with the blood of the subject. The formulation is presented in unit or multi-dose containers, such as sealed ampoules or vials. The formulation is delivered by any mode of injection, including, without limitation, epifascial, intracapsular, intracranial, intracutaneous, intrathecal, intramuscular, intraorbital, intraperitoneal, intraspinal, intrasternal, intravascular, intravenous, parenchymatous, subcutaneous, or sublingual or by way of catheter into the subject's heart.

Pharmaceutical compositions for rectal or vaginal administration can be suppositories, and those for per- or transcutaneous administration include powders, aerosols, creams, ointments, gels, and patches.

For transdermal administration, the compounds can be combined with skin penetration enhancers, such as propylene glycol, polyethylene glycol, isopropanol, ethanol, oleic acid, or N-methylpyrrolidone. These agents increase the permeability of the skin and permit compounds to penetrate through the skin and into the bloodstream. The compound/enhancer compositions can be further combined with a polymeric substance, such as ethylcellulose, hydroxypropyl cellulose, ethylene/vinylacetate, or polyvinyl pyrrolidone to provide the composition in gel form, which is dissolved in a solvent, evaporated to the desired viscosity, and then applied to backing material to provide a patch.

A pharmaceutically-acceptable excipient can be present in a pharmaceutical composition at a mass of between about 0.1% and about 99% by mass of the composition. For example, a pharmaceutically-acceptable excipient can be present in a pharmaceutical composition at a mass of between about 0.1% and about 95%, between about 0.11% and about 90%, between about 0.1% and about 85%, between about 0.1% and about 80%, between about 0.1% and about 75%, between about 0.1% and about 70%, between about 0.1% and about 65%, between about 0.1% and about 60%, between about 0.1% and about 55%, between about 0.1% and about 50%, between about 0.1% and about 45%, between about 0.11% and about 40%, between about 0.1% and about 35%, between about 0.1% and about 30%, between about 0.1% and about 25%, between about 0.1% and about 20%, between about 0.1% and about 15%, between about 0.1% and about 10%, between about 0.1% and about 5%, between about 0.1% and about 1%, by mass of the formulation.

A pharmaceutically-acceptable excipient can be present at about 0.1%, 0.2%, 0.3%, 0.4%, 0.5%, 0.6%, 0.7%, 0.8%, 0.9%, 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 99.1%, about 99.2%, about 99.3%, about 99.4%, about 99.5%, about 99.6%, about 99.7%, about 99.8%, or about 99.9% by mass of the formulation.

In accordance with the methods of the present disclosure, any of these compounds can be administered to the subject (or contacted with cells of the subject) in an amount effective to limit or prevent a decrease in the level of RyR-bound Calstabin in the subject, particularly in cells of the subject.

Alternatively, the methods of the present disclosure comprise administering a compound in an amount effective to treat or prevent a RyR-related condition as described herein.

In some embodiments, a suitable amount of the compounds effective to limit or prevent a decrease in the level of RyR-bound Calstabin in the subject and/or to treat or prevent conditions associated with RyR ranges from about 100 to about 500 mg per day, for example about 100 mg per day, about 120 mg per day, about 140 mg per day, about 160 mg per day, about 180 mg per day, about 200 mg per day, about 220 mg per day, about 240 mg per day, about 260 mg per day, about 280 mg per day, about 300 mg per day, about 320 mg per day, about 340 mg per day, about 360 mg per day, about 380 mg per day, about 400 mg per day, about 420 mg per day, about 440 mg per day, about 460 mg per day, about 480 mg per day or about 500 mg per day.

A compound described herein can be present in a composition in a range of from about 1 mg to about 2000 mg; from about 1 mg to about 1000 mg; from about 1 mg to about 500 mg; from about 5 mg to about 1000 mg, from about 5 mg to about 500 mg, from about 5 mg to about 100 mg, from about 10 mg to about 50 mg, from about 50 mg to about 250 mg, from about 100 mg to about 200 mg, from about 1 mg to about 50 mg, from about 50 mg to about 100 mg, from about 100 mg to about 150 mg, from about 150 mg to about 200 mg, from about 200 mg to about 250 mg, from about 250 mg to about 300 mg, from about 300 mg to about 350 mg, from about 350 mg to about 400 mg, from about 400 mg to about 450 mg, from about 450 mg to about 500 mg, from about 500 mg to about 550 mg, from about 550 mg to about 600 mg, from about 600 mg to about 650 mg, from about 650 mg to about 700 mg, from about 700 mg to about 750 mg, from about 750 mg to about 800 mg, from about 800 mg to about 850 mg, from about 850 mg to about 900 mg, from about 900 mg to about 950 mg, or from about 950 mg to about 1000 mg.

A compound described herein can be present in a composition in an amount of about 1 mg, about 2 mg, about 3 mg, about 4 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 125 mg, about 150 mg, about 175 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1900 mg, about 1950 mg, or about 2000 mg.

In some embodiments, a dose can be expressed in terms of an amount of the drug divided by the mass of the subject, for example, milligrams of drug per kilograms of subject body mass. In some embodiments, a compound is administered in an amount ranging from about 5 mg/kg to about 50 mg/kg, about 250 mg/kg to about 2000 mg/kg, about 10 mg/kg to about 800 mg/kg, about 50 mg/kg to about 400 mg/kg, about 100 mg/kg to about 300 mg/kg, or about 150 mg/kg to about 200 mg/kg.

In some embodiments, the therapeutically-effective dose is between about 100 mg to about 200 mg per day. In some embodiments, the therapeutically-effective dose is 200 mg per day. In some embodiments, the therapeutically-effective dose is 120 mg per day.

Example 1: Preparation of 4-[(7-methoxy-2,3-dihydro-1,4-benzothiazepin-4(5H)yl)methyl]benzoic acid 4-[(7-methoxy-2,3-dihydro-1,4-benzothiazepin-4(5H)yl) methyl]benzoic acid was prepared as described below.

Stage 1: 7-methoxy-2,3,4,5-tetrahydrobenzo[f][1,4] thiazepine ("Amine")

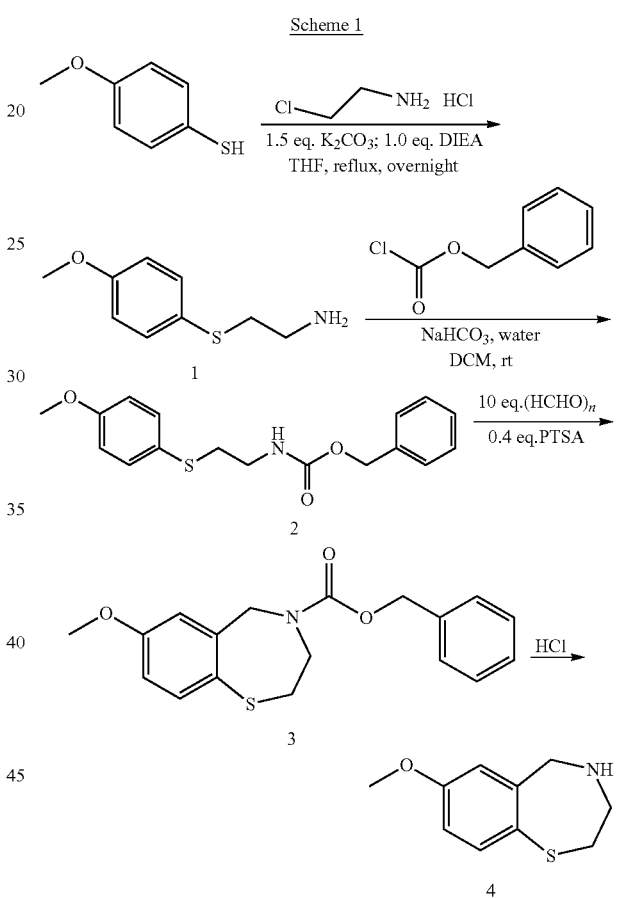

Scheme 1

2-(4-Methoxyphenylthio)ethanamine (1)

4-Methoxythiophenol (50 g, 0.357 mol), 2-chloroethylamine monohydrochloride (39.8 g, 0.343 mol.), K$_2$CO$_3$ (78.8 g, 0.57 mol) and diisopropyl ethylamine (32 mL, 0.178 mol) were mixed in tetrahydrofuran (THF). The mixture was degassed for 5 min. under reduced pressure and heated at reflux under argon overnight. The solvent was removed and water was added to the flask. The mixture was extracted with dichloromethane. The organic layers were collected, dichloromethane was removed and conc. HCl was added, followed by of water. The solution was extracted with 1:1 ethyl acetate (EtOAc)/hexane. The aqueous layer was adjusted to pH 10 with 2 M NaOH, and was extracted with dichloromethane. The combined organic solution was dried over anhydrous sodium sulfate. Removal of solvent provided the target compound.

Benzyl 2-(4-methoxyphenylthio)ethylcarbamate (2)

To a flask containing compound 1 (8.0 g, 43.7 mmol), sodium bicarbonate (12.1 g, 144 mmol), water, and dichloromethane was added benzyl chloroformate (8.2 g, 48.1 mmol, diluted in 100 mL of dichloromethane) dropwise at 0° C. After the addition, the mixture was stirred at r.t. for 5 hr. The organic layer was collected and the aqueous solution was extracted with 100 mL of dichloromethane. The combined organic solution was dried over sodium sulfate. The solvent was removed and the resulting solid was triturated with THF/hexane (1:10). The solid was collected and dried leaving the target product.

Benzyl 7-methoxy-2,3-dihydrobenzo[f][1,4]thiazepine-4(5H)-carboxylate (3)

A mixture of compound 2 (7.3 g, 23 mmol), paraformaldehyde (6.9 g 0.23 mol), and p-toluenesulfonic acid (1.45 g, 7.6 mmol) in toluene was stirred at 70° C. overnight. After cooling to r.t., the solid was filtered off. The solution was extracted with saturated sodium carbonate, and the organic layer was dried over anhydrous sodium sulfate to yield the target product as a liquid after removal of the solvent.

7-Methoxy-2,3,4,5-tetrahydrobenzo[f][1,4]thiazepine hydrobromide (Amine)

Compound 3 (10 g, 30 mmol) was mixed with concentrated HCl, water and dioxane. The mixture was stirred at 100° C. overnight. After cooling to room temperature, most of the solvent and HCl were removed under reduced pressure. Water was added to the solution and the solid was filtered off. The aqueous solution was extracted with EtOAc/hexane (1:1) and basified by adding 15 g of NaOH. The mixture was extracted with dichloromethane. The combined solution was dried over anhydrous sodium sulfate. Removal of solvent provided a liquid that solidified after standing at room temperature (r.t.), to yield the target compound.

Stage 2: -[(7-methoxy-2,3-dihydro-1,4-benzothiazepin-4(5H)yl)methyl]benzoic acid

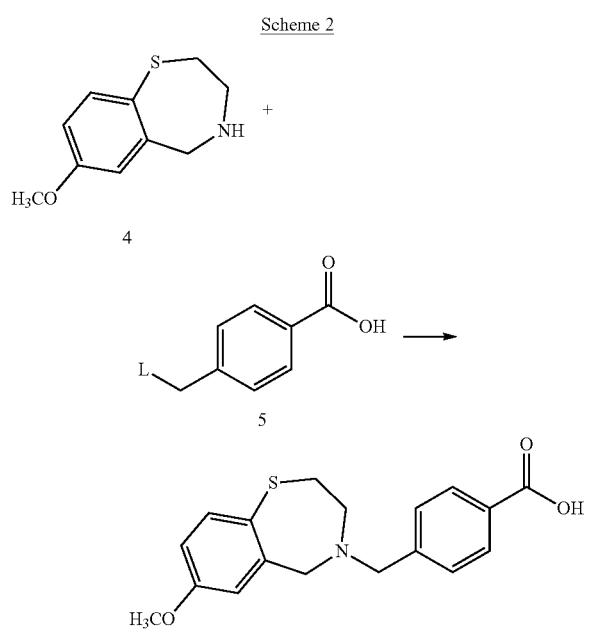

Scheme 2

In Scheme 2, L is a leaving group, which is, by way of example, a halogen or a sulfonate (OSO$_2$R' wherein R' is alkyl or aryl, e.g., OMs (mesylate) or OTs (tosylate)). Amine (4) (1 mmol) was dissolved dichloromethane. To the solution was added alkylation reagent (5) (1 mmol), followed by N,N-diisopropylethylamine (2 mmol). The mixture was stirred at room temperature overnight. The solution was loaded onto a silica gel column directly and eluted with hexane/EtOAc (2:1, v/v) to afforded the desired product.

Example 2: Preparation of 4-[(7-methoxy-2,3-dihydro-1,4-benzothiazepin-4(5H)yl)methyl]benzoic acid hemifumarate—Form 1

4-[(7-methoxy-2,3-dihydro-1,4-benzothiazepin-4(5H)yl)methyl]benzoic acid was prepared as in Example 1. To form the hemifumarate salt, 4-[(7-methoxy-2,3-dihydro-1,4-benzothiazepin-4(5H)yl)methyl]benzoic acid was salified with fumaric acid in the presence of isopropanol, as depicted in Scheme 3. After cooling, the obtained product was filtered and washed with isopropanol to give the title product.

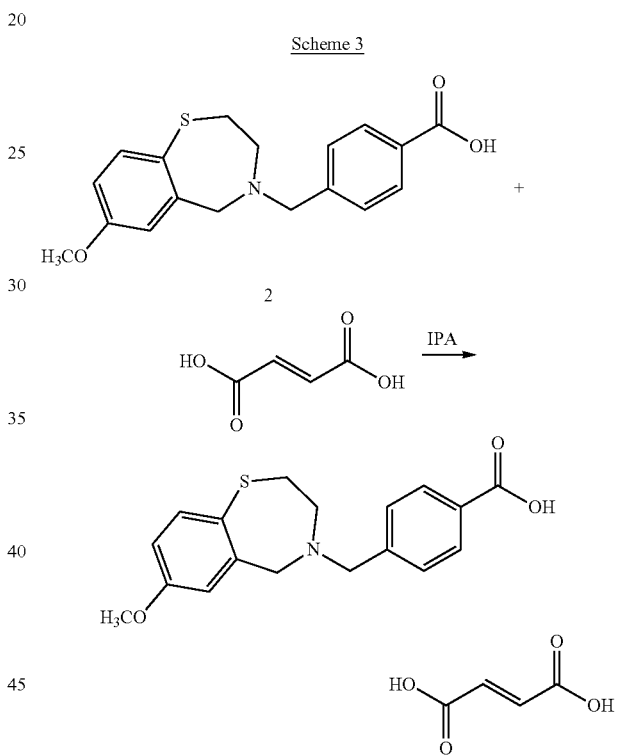

Scheme 3

Form 1 can optionally be ground to a particle size distribution described in Table 3.

TABLE 3

| Particle size | |
|---|---|
| D(v, 0.1) | 3.4 μm ≤ D(v,0.1) ≤ 4.4 μm |
| -D(v, 0.5) | 6.9 μm ≤ D(v,0.5) ≤ 9.75 μm |
| -D(v, 0.9) | 13.4 μm ≤ D(v,0.9) ≤ 19.5 μm |

Example 3: Preparation of 4-[(7-methoxy-2,3-dihydro-1,4-benzothiazepin-4(5H)yl)methyl]benzoic acid hemifumarate—Form 2

4-[(7-methoxy-2,3-dihydro-1,4-benzothiazepin-4(5H)yl)methyl]benzoic acid was prepared as in Example 1. To form the hemifumarate salt, 4-[(7-methoxy-2,3-dihydro-1,4-benzothiazepin-4(5H)yl)methyl]benzoic acid was salified with fumaric acid in the presence of a mixture of dimethylsulfoxide and water, as depicted in Scheme 4. After cooling, the obtained product was filtered and washed with water and acetone to give the desired product.

Scheme 4

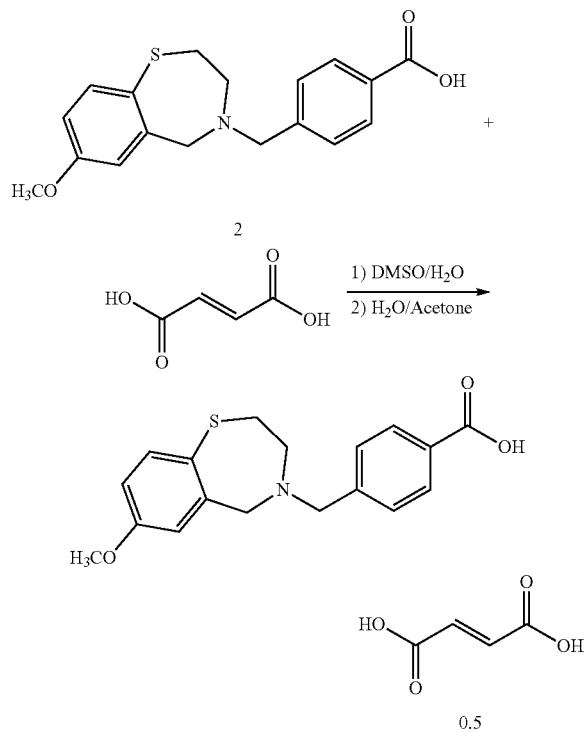

Form 2 can optionally be ground to a particle size distribution described in Table 4.

TABLE 4

| Particle size | |
|---|---|
| -D(v, 0.5) | 10 μm ≤ D(v,0.5) ≤ 30 μm |
| -D(v, 0.9) | ≤90 μm |

Example 4: Stability of 4-[(7-methoxy-2,3-dihydro-1,4-benzothiazepin-4(5H)yl)methyl]benzoic acid hemifumarate Form 1 and Form 2

Figure 5:
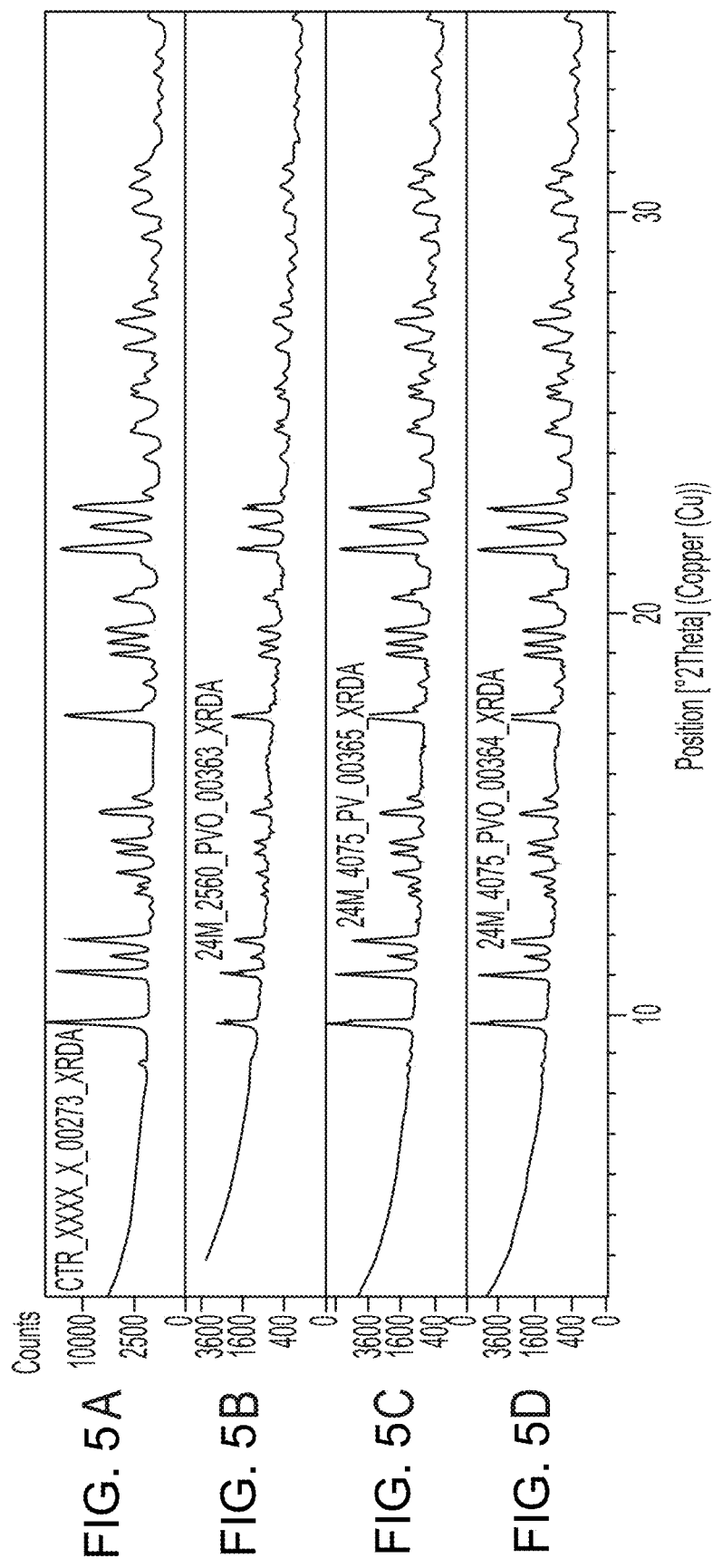
FIG. 5 depicts a characteristic X-ray diffraction (XRD) pattern of 4-[(7-methoxy-2,3-dihydro-1,4-benzothiazepin-4 (5H)yl)methyl]benzoic acid hemifumarate Form 1 at inception (top panel) and after 24 months (bottom three panels).

Form 1 was stable after 24 months as shown in FIG. 5. The top panel depicts the polymorph at initiation and the bottom three panels depict the polymorph after 24 months. FIG. 5 Panel A: initial control; FIG. 5 Panel B: sample stored for 2 years in open bottle in stability chambers at 25° C./60% relative humidity (RH); FIG. 5 Panel C: sample stored for 2 years in closed bottle in stability chambers at 40° C./75% RH; FIG. 5 Panel D: sample stored for 2 years in open bottle in stability chambers at 40° C./75% RH.

Figure 10:
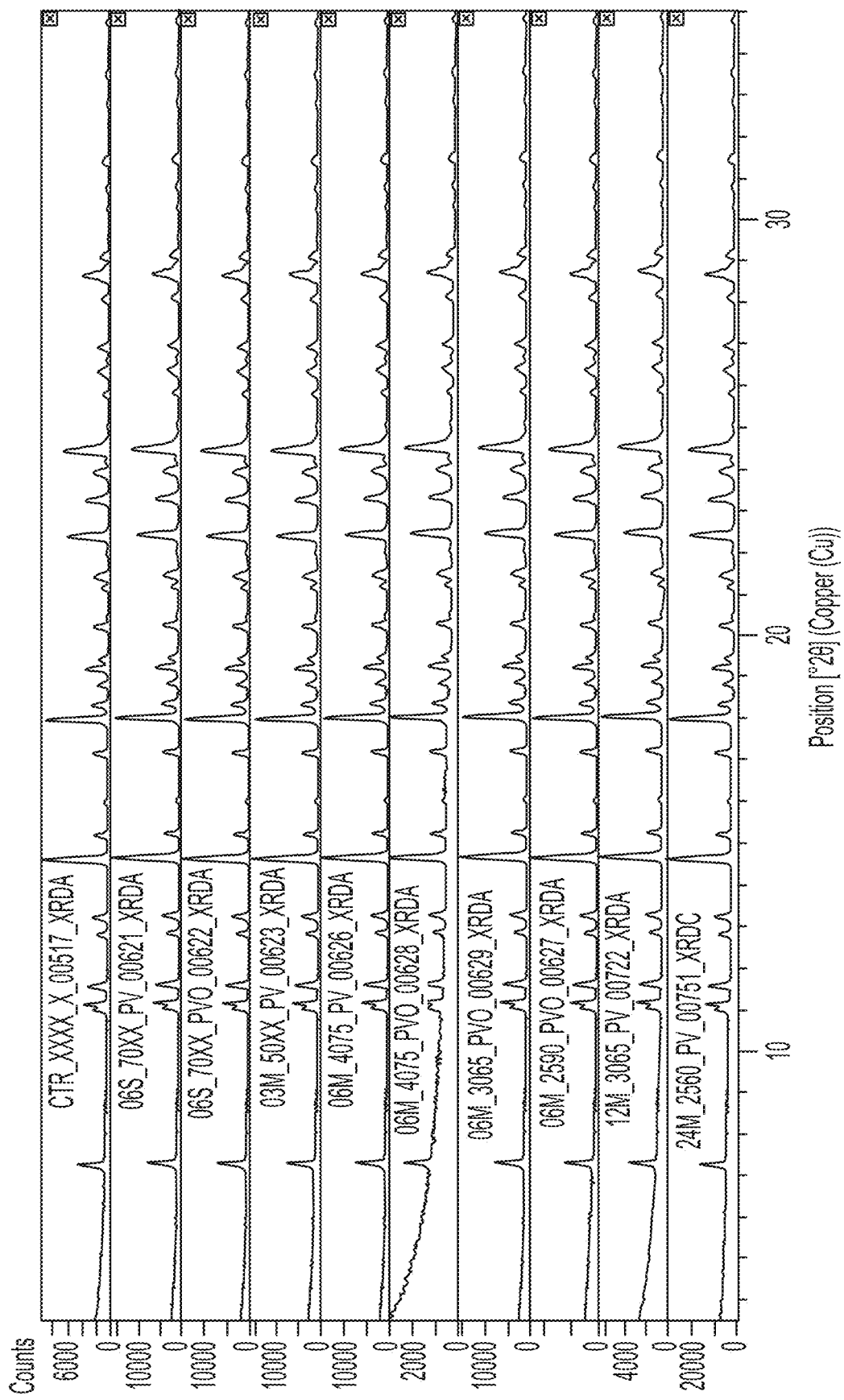
FIG. 10 depicts a characteristic X-ray diffraction (XRD) pattern of 4-[(7-methoxy-2,3-dihydro-1,4-benzothiazepin-4

Form 2 was stable after 24 months as shown in FIG. 10. The top panel depicts the polymorph at initiation and the bottom panels depict the polymorph after 3, 6, 12 and 24 months.

Competitive slurry experiments were performed at 15° C. (Table 5) or 40° C. (Table 6) by mixing Form 1 and Form 2 in various solvents in acetonitrile/water, acetone/water and methanol/water mixtures. In methanol/water mixtures, slurries of Form 1 and Form 2 converted into the methanol solvate (Form 3) in all tested solvent mixture ratios either at 15° C. or 40° C., except in methanol/water (20/80 v/v) in which a mixture of Form 2 and methanol solvate was observed. In acetonitrile/water mixtures, slurries of Form 1 and Form 2 converted into the acetonitrile solvate (Form 4) in all tested solvent mixture ratios either at 15° C. (Table 5) or 40° C. (Table 6). In acetone/water mixtures, slurries of Form 1 and Form 2 converted into Form 2 in all tested conditions. Based on the results, water, acetone or water/acetone mixtures resulted in crystalline Form 2.

TABLE 5

Results of competitive slurry experiments at 15° C. for 10 days

| Solvent | XRD |
|---|---|
| Water | Form 2 |
| Methanol/water 20/80 | Form 2 + Methanol solvate |
| Methanol/water 50/50 | Methanol solvate (Form 3) |
| Methanol/water 70/30 | Methanol solvate (Form 3) |
| Methanol/water 95/5 | Methanol solvate (Form 3) |
| Methanol | Methanol solvate (Form 3) |
| Acetonitrile/water 15/85 | Acetonitrile solvate (Form 4) |
| Acetonitrile/water 87/13 | Acetonitrile solvate (Form 4) |
| Acetonitrile/water 94/6 | Acetonitrile solvate (Form 4) |
| Acetonitrile/water 98/2 | Acetonitrile solvate (Form 4) |
| Acetonitrile | Acetonitrile solvate (Form 4) |
| Acetone/water 30/70 | Form 2 |
| Acetone/water 90/10 | Form 2 |
| Acetone/water 96/4 | Form 2 |
| Acetone/water 98/2 | Form 2 |
| Acetone | Form 2 |

TABLE 6

Results of competitive slurry experiments at 40° C. for 5 days

| Solvent | XRD |
|---|---|
| Water | Form 2 |
| Methanol/water 20/80 | Form 2 + Methanol solvate |
| Methanol/water 50/50 | Methanol solvate (Form 3) |
| Methanol/water 70/30 | Methanol solvate (Form 3) |
| Methanol/water 95/5 | Methanol solvate (Form 3) |
| Methanol | Methanol solvate (Form 3) |
| Acetonitrile/water 15/85 | Acetonitrile solvate (Form 4) |
| Acetonitrile/water 87/13 | Acetonitrile solvate (Form 4) |
| Acetonitrile/water 94/6 | Acetonitrile solvate (Form 4) |
| Acetonitrile/water 98/2 | Acetonitrile solvate (Form 4) |
| Acetonitrile | Acetonitrile solvate (Form 4) |
| Acetone/water 30/70 | Form 2 |
| Acetone/water 90/10 | Form 2 |
| Acetone/water 96/4 | Form 2 |
| Acetone/water 98/2 | Form 2 |
| Acetone | Form 2 |

In these experiments, Form 2 was more stable than Form 1 was. DSC analyses indicated both a higher melting point and a larger enthalpy of fusion of Form 2 than Form 1 (compare FIGS. 2 and 7), and support the conclusion that Form 2 is more stable than Form 1 is. However, Form 1 can be stored for at least 24 months without any detectable conversion into Form 2 (FIG. 5).

Example 5: Stability of 4-[(7-methoxy-2,3-dihydro-1,4-benzothiazepin-4(5H)yl)methyl]benzoic acid hemifumarate Form 2

Stability of 4-[(7-methoxy-2,3-dihydro-1,4-benzothiazepin-4(5H)yl)methyl]benzoic acid hemifumarate Form 2 was evaluated for up to 24 months under various conditions. The results are shown in Tables 7-10.

TABLE 7 stability in an airtight glass bottle after storage at −18° C.

| Parameters tested | Storage period at −18° C. | | | | | | | |
|---|---|---|---|---|---|---|---|---|
| | T0 | 6 W | 3 M | 6 M | 9 M | 1 Y | 18 M | 2 Y |
| Appearance | A1 | A1 | A1 | A1 | A1 | A1 | A1 | A1 |
| Identification | I1 | I3 | — | — | — | — | — | — |
| Water content (%) | 0.1 | 0.1 | 0.1 | 0.1 | <0.1 | <0.1 | 0.1 | <0.1 |
| Related substances content (LC) Sum of impurities (%) | ≤0.05 | — | — | — | — | — | — | — |
| Assay of Drug substance (LC) (%) | 99.7 | — | — | — | — | — | — | — |
| Assay by potentiometry (%) | 99.9 | 99.9 | — | — | 99.7 | — | — | — |

—: Control not scheduled

A1: White or almost white powder

I1: Spectrum of test sample identical to spectrum of reference sample

I3: Spectrum of test sample identical to spectrum of reference sample stored at −18° C.

TABLE 8 stability in an airtight glass bottle after storage at 25° C./60% RH

| Parameters tested | Storage period at 25° C. 60% RH | | | | | | | |
|---|---|---|---|---|---|---|---|---|
| | T0 | 6 W | 3 M | 6 M | 9 M | 1 Y | 18 M | 2 Y |
| Appearance | A1 | A1 | A1 | A1 | A1 | A1 | A1 | A1 |
| Identification | I1 | I3 | I3 | I3 | I3 | I3 | I3 | I3 |
| Water content (%) | 0.1 | <0.1 | 0.1 | 0.1 | <0.1 | <0.1 | 0.1 | <0.1 |
| Related substances content (LC) Sum of impurities (%) | ≤0.05 | ≤0.05 | ≤0.05 | ≤0.05 | ≤0.05 | ≤0.05 | ≤0.05 | ≤0.05 |
| Assay of Drug substance (LC) (%) | 99.7 | 102.5 | 99.6 | 99.7 | 100.6 | 99.8 | 100.9 | 99.5 |
| Assay by potentiometry (%) | 99.9 | 99.7 | 100.0 | 102.1 | 99.1 | — | 99.8 | 99.6 |

—: Control not scheduled

A1: White or almost white powder

I1: Spectrum of test sample identical to spectrum of reference sample

I3: Spectrum of test sample identical to spectrum of reference sample stored at −18° C.

TABLE 9 stability in an airtight glass bottle after storage at 30° C./65% RH

| Parameters tested | Storage period at 30° C. 65% RH | | | | | |
|---|---|---|---|---|---|---|
| | T0 | 6 W | 3 M | 6 M | 9 M | 1 Y |
| Appearance | A1 | A1 | A1 | A1 | A1 | A1 |
| Identification | I1 | I3 | I3 | I3 | I3 | I3 |
| Water content (%) | 0.1 | <0.1 | 0.1 | 0.1 | <0.1 | <0.1 |
| Related substances content (LC) Sum of impurities (%) | ≤0.05 | ≤0.05 | ≤0.05 | ≤0.05 | ≤0.05 | ≤0.05 |
| Assay of Drug substance (LC) (%) | 99.7 | 102.4 | 99.7 | 100.2 | 99.7 | 99.5 |
| Assay by potentiometry (%) | 99.9 | 99.8 | 99.8 | 100.4 | 99.6 | — |

—: Control not scheduled

A1: White or almost white powder

I1: Spectrum of test sample identical to spectrum of reference sample

I3: Spectrum of test sample identical to spectrum of reference sample stored at −18° C.

TABLE 10 stability in an airtight glass bottle after storage at 40° C./75% RH

| | Storage period at 40° C. 75% RH | | | |
|---|---|---|---|---|
| Parameters tested | T0 | 6 W | 3M | 6M |
| Appearance | A1 | A1 | A1 | A1 |
| Identification | I1 | I3 | I3 | I3 |
| Water content (%) | 0.1 | 0.1 | 0.1 | 0.1 |
| Related substances content (LC) . Sum of impurities (%) | ≤0.05 | ≤0.05 | ≤0.05 | ≤0.05 |
| Assay of Drug substance (LC) (%) | 99.7 | 102.2 | 99.5 | 99.2 |
| Assay by potentiometry (%) | 99.9 | 99.8 | 99.8 | 100.5 |

A1: White or almost white powder
I1: Spectrum of test sample identical to spectrum of reference sample
I3: Spectrum of test sample identical to spectrum of reference sample stored at −18° C.

Example 6: Methods

XRD: Measurement conditions are described in Table 11.

TABLE 11

| Raw Data Origin | XRD measurement (*.XRDML) |
|---|---|
| Scan Axis | Gonio |
| Start Position [° 2θ] | 3.0034 |
| End Position [° 2θ] | 54.9894 |
| Step Size [° 2θ] | 0.0170 |
| Scan Step Time [s] | 34.9250 |
| Scan Type | Continuous |
| PSD Mode | Scanning |
| PSD Length [° 2θ] | 2.12 |
| Offset [° 2θ] | 0.0000 |
| Divergence Slit Type | Fixed |
| Divergence Slit Size [°] | 0.4354 |
| Specimen Length [mm] | 10.00 |
| Measurement Temperature [° C.] | 25.00 |
| Anode Material | Cu |
| K-Alpha1 [Å] | 1.54060 |
| K-Alpha2 [Å] | 1.54443 |
| K-Beta [Å] | 1.39225 |
| K-A2/K-A1 Ratio | 0.50000 |
| Generator Settings | 40 mA, 45 kV |
| Diffractometer Type | 0000000000005660 |
| Diffractometer Number | 0 |
| Goniometer Radius [mm] | 240.00 |
| Dist. Focus-Diverg. Slit [mm] | 100.00 |
| Incident Beam Monochromator | No |
| Spinning | Yes |

Peak Search
The peak search was performed with Highscore Plus v4.6. The following parameters were applied for the automatic peak search:
Minimum significance="1"
Minimum tip width="0.01"
Maximum tip width="1"
Peak base width="2"
Method="Top of smoothed peak"
After a default profile fitting was performed, undetected peaks were added manually. Default profile fittings were then performed again.
Calibration
The calibration and qualification of XRD instrument was performed once a year with a full qualification in reflexion mode and a linearity check in transmission mode.
Qualification in Reflexion Mode:
Linearity: Performed on a Panalytical 640 Silicium tablet reference sample at the following angles: 28.441°, 47.300°, 56.119°, 69.126°, 76.372°, 88.025°, 94.946°, 106.701° and 114.083° 2Theta. Linearity coefficient was less than or equal to 0.03° 2theta.

Quantitative analysis: waser formed on NIST sintered alumina disc at the following angles: 25.6°, 35.1°, 43.4°, 52.5°, 57.5°, 76.9° et and 77.2°, 89.0° and 101.1° 2Theta. The relative intensity for each diffraction peak was less than or equal to 14% compared to theoretical values given by NIST.

Resolution: Performed on NIST sintered alumina disc at the following angle: 57.5° 2Theta. The result was less than or equal to 0.09° 2 Theta Linearity check in transmission mode: Performed on a NIST Silicium powder reference at the following angles: 28.441°, 47.300°, 56.119°, 69.126° and 76.372° 2Theta Linearity coefficient was less than or equal to 0.03° 2theta.

Thermal Analysis—Differential Scanning Calorimetry
Melting points were measured by differential scanning calorimetry (DSC). DSC was performed by (a) equilibrating a sample of a crystalline form of 4-[(7-methoxy-2,3-dihydro-1,4-benzothiazepin-4(5H)yl)methyl]benzoic acid hemifumarate at 20° C.; and (b) increasing the temperature at 10° C./minute to 250° C., using a DSC Q1000 or DSC Q2000 differential scanning calorimetry instrument.

Thermal Analysis—Thermogravimetric Analysis
Thermogravimetric analysis (TGA) was performed. A 10 to 20 mg of sample of a crystalline form of 4-[(7-methoxy-2,3-dihydro-1,4-benzothiazepin-4(5H)yl)methyl]benzoic acid hemifumarate was placed into an aluminum pan, with nitrogen purge. The sample was equilibrated at 25° C. in a temperature-controlled chamber. The sample was heated at a scan rate of about 10° C./minute to 250° C. under nitrogen purge. A TGA Q5000 thermogravimetric analysis instrument was used.

Thermal Analysis—Dynamic Vapor Sorption
Dynamic vapor sorption (DVS) analysis was performed by measuring mass variation of the crystalline form of 4-[(7-methoxy-2,3-dihydro-1,4-benzothiazepin-4(5H)yl) methyl]benzoic acid hemifumarate as a function of relative humidity using a DVS intrinsic instrument. A 5 mg to 10 mg of a sample of a crystalline form of 4-[(7-methoxy-2,3-dihydro-1,4-benzothiazepin-4(5H)yl)methyl]benzoic acid, hemifumarate was placed into a sample pan of a DVS intrinsic instrument at 25° C. under controlled humidity. The mass variation was recorded as a function of relative humidity.

Measurement of DVS comprised: (a) equilibrating a sample of the crystalline form at 25° C. and 50% relative humidity in a temperature-controlled and humidity controlled chamber until mass variation is less than 0.002% per minute for 6 hours; (b) increasing the relative humidity from 50% to 90% at a rate of 10% per hour; (c) equilibrating the sample at 90% relative humidity until mass variation of less than 0.002% per minute for 6 hours is observed; (d) decreasing the relative humidity from 90% to 0% at a rate of 10% per hour; (e) equilibrating the sample at 0% relative humidity until mass variation of less than 0.002% per minute for 6 hours is observed; and (f) increasing the relative humidity from 0% to 50% at a rate of 10% per hour.

Incorporation by Reference

All publications, patents, and patent applications mentioned in this specification are herein incorporated by reference to the same extent as if each individual publication, patent, or patent application was specifically and individually indicated to be incorporated by reference.

EMBODIMENTS

Embodiment 1. A composition comprising a crystalline form of 4-[(7-methoxy-2,3-dihydro-1,4-benzothiazepin-4

(5H)yl)methyl]benzoic acid hemifumarate, wherein if a melting point of the crystalline form is obtained by:
(a) equilibrating a sample of said crystalline form at a temperature of about 20° C. in a temperature-controlled chamber; and
(b) increasing the temperature of the temperature-controlled chamber at a scan rate of about 10° C./minute to 250° C. using a differential scanning calorimetry instrument,
then a melting point of 201-203° C. ($T_{onset}$) is obtained Embodiment 2. The composition of embodiment 1, wherein the crystalline form of 4-[(7-methoxy-2,3-dihydro-1,4-benzothiazepin-4(5H)yl)methyl]benzoic acid hemifumarate is characterized by a differential scanning calorimetry profile substantially as shown in FIG. 2.

Embodiment 3. The composition of embodiment 1 or 2, wherein if an X-ray diffraction pattern of the crystalline form is obtained using measurement conditions, the measurement conditions comprising:

| | |
|---|---|
| Start Position [° 2θ] | 3.00 |
| End Position [° 2θ] | 54.99 |
| Step Size [° 2θ] | 0.018 |
| Scan Step Time [s] | 34.92 |
| Measurement Temperature [° C.] | 25.00 |
| K-Alpha1 [Å] | 1.54 |
| K-Alpha2 [Å] | 1.54 |
| K-Beta [Å] | 1.39 |
| Spinning | Yes | then at least two X-ray diffraction peaks selected from 9.8±0.1, 11.8±0.1, 13.5±0.1, 14.0±0.1, 14.3±0.1, 17.4±0.1, 18.9±0.1, 19.6±0.1, 22.1±0.1, 26.6±0.1, and 27.2±0.1 degrees two theta (°θ) are observed.

Embodiment 4. The composition of embodiment 3, wherein X-ray diffraction peaks at 9.8±0.1, 11.0±0.1, 17.4±0.1, 21.6±0.1 and 22.6±0.1 degrees two theta (°θ) are observed.

Embodiment 5. The composition of embodiment 3 or 4, wherein X-ray diffraction peaks at 9.8±0.1, 11.0±0.1, 11.8±0.1, 15.0±0.1, 17.4±0.1, 21.6±0.1, 22.1±0.1, and 22.6±0.1 degrees two theta (°θ) are observed.

Embodiment 6. composition of any one of embodiments 3-5, wherein X-ray diffraction peaks at 9.8±0.1, 11.0±0.1, 11.4±0.1, 11.8±0.1, 13.5±0.1, 14.0±0.1, 14.3±0.1, 15.0±0.1, 17.4±0.1, 18.9±0.1, 19.3±0.1, 19.6±0.1, 20.3±0.1, 21.6±0.1, 22.1±0.1, 22.6±0.1, 26.6±0.1, and 27.2±0.1 degrees two theta (°θ) are observed.

Embodiment 7. The composition of any one of embodiments 3-6, wherein X-ray diffraction peaks substantially as shown in FIG. 1 are observed.

Embodiment 8. The composition of any one of embodiments 1-7, wherein if a thermogravimetric analysis of the crystalline form is obtained by:
(a) equilibrating a sample of said crystalline form at 25° C. in a temperature-controlled chamber; and
(b) increasing the temperature at a scan rate of about 10° C./minute to 250° C. using a thermogravimetric analysis instrument,
then a thermogravimetric analysis profile substantially as shown in FIG. 3 is obtained.

Embodiment 9. The composition of any one of embodiments 1-8, wherein if a dynamic vapor sorption profile of the crystalline form is obtained by:
(a) equilibrating a sample of said crystalline form at 25° C. and 50% relative humidity in a temperature-controlled and humidity-controlled chamber until mass variation of less than 0.002% per minute for 6 hours is obtained;
(b) increasing the relative humidity from 50% to 90% at a rate of 10% per hour;
(c) equilibrating the sample at 90% relative humidity until mass variation of less than 0.002% per minute for 6 hours is obtained;
(d) decreasing the relative humidity from 90% to 0% at a rate of 10% per hour;
(e) equilibrating the sample at 0% relative humidity until mass variation of less than 0.002% per minute for 6 hours is observed; and
(f) increasing the relative humidity from 0% to 50% at a rate of 10% per hour,
then a dynamic vapor sorption profile substantially as shown in FIG. 4 is obtained.

Embodiment 10. The composition of any one of embodiments 1-9, wherein the crystalline form is substantially anhydrous.

Embodiment 11. The composition of any one of embodiments 1-10, wherein the crystalline form comprises a population of particles, wherein at least about 90% by mass of the particles comprise a diameter of no greater than about 20 microns.

Embodiment 12. The composition of any one of embodiments 1-10, wherein the crystalline form comprises a population of particles, wherein at least about 50% by mass of the particles comprise a diameter of no greater than 10 microns.

Embodiment 13. The composition of any one of embodiments 1-10, wherein the crystalline form comprises a population of particles, wherein at least about 50% by mass of the particles comprise a diameter of between about 6.9 microns and about 9.75 microns.

Embodiment 14. A composition comprising a crystalline form of 4-[(7-methoxy-2,3-dihydro-1,4-benzothiazepin-4(5H)yl)methyl]benzoic acid hemifumarate, wherein the crystalline form is characterized by a melting point of 201-203° C. ($T_{onset}$).

Embodiment 15. A composition comprising a crystalline form of 4-[(7-methoxy-2,3-dihydro-1,4-benzothiazepin-4(5H)yl)methyl]benzoic acid hemifumarate, wherein the crystalline form is characterized by an X-ray diffraction pattern comprising least two X-ray diffraction peaks selected from 9.8±0.1, 11.8±0.1, 13.5±0.1, 14.0±0.1, 14.3±0.1, 17.4±0.1, 18.9±0.1, 19.6±0.1, 22.1±0.1, 26.6±0.1, and 27.2±0.1 degrees two theta (°θ).

Embodiment 16. A process for synthesis of a crystalline form of 4-[(7-methoxy-2,3-dihydro-1,4-benzothiazepin-4(5H)yl)methyl]benzoic acid hemifumarate, the process comprising:
a. reacting 4-[(7-methoxy-2,3-dihydro-1,4-benzothiazepin-4(5H)yl)methyl]benzoic acid or an ionized form thereof with fumaric acid in presence of isopropanol to generate a reaction mixture, the reaction mixture comprising a precipitate;
b. isolating the precipitate from a.;
c. washing the precipitate from b. with isopropanol; and
d. drying the precipitate from c. to obtain particles, the particles comprising the crystalline form of 4-[(7-methoxy-2,3-dihydro-1,4-benzothiazepin-4(5H)yl)methyl]benzoic acid hemifumarate,
wherein if a melting point of the crystalline form is obtained by: (a) equilibrating a sample of said crystalline form at a temperature of about 20° C. in a temperature-controlled chamber; and (b) increasing the temperature of the temperature-controlled chamber at a scan rate of about 10° C./minute to 250° C. using a differential scanning calorimetry instrument, then a melting point of 201-203° C. ($T_{onset}$) is obtained.

Embodiment 17. The process of embodiment 16, further comprising:
(i) cooling the reaction mixture generated in a., wherein (i) is performed prior to b.

Embodiment 18. The process of embodiment 16 or 17, further comprising measuring particle size of the particles comprising the crystalline form of 4-[(7-methoxy-2,3-dihydro-1,4-benzothiazepin-4(5H)yl)methyl]benzoic acid hemifumarate.

Embodiment 19. The process of any one of embodiments 16-18, further comprising reducing the particle size of the particles comprising crystalline form of 4-[(7-methoxy-2,3-dihydro-1,4-benzothiazepin-4(5H)yl)methyl]benzoic acid hemifumarate.

Embodiment 20. The process of embodiment 19, wherein the crystalline form comprises a population of particles, wherein at least about 90% by mass of the particles comprise a diameter of no greater than about 20 microns.

Embodiment 21. The process of embodiment 19, wherein the crystalline form comprises a population of particles, wherein at least about 50% by mass of the particles comprise a diameter of no greater than about 10 microns.

Embodiment 22. The process of embodiment 19, wherein the crystalline form comprises a population of particles, wherein at least about 50% by mass of the particles comprise a diameter of between about 6.9 microns and about 9.75 microns.

Embodiment 23. A process for synthesis of a crystalline form of 4-[(7-methoxy-2,3-dihydro-1,4-benzothiazepin-4(5H)yl)methyl]benzoic acid hemifumarate having a melting point of 201-203° C. ($T_{onset}$), the process comprising:
a. reacting 4-[(7-methoxy-2,3-dihydro-1,4-benzothiazepin-4(5H)yl)methyl]benzoic acid or an ionized form thereof with fumaric acid in presence of isopropanol to generate a reaction mixture, the reaction mixture comprising a precipitate;
b. isolating the precipitate from a.;
c. washing the precipitate from b. with isopropanol; and
d. drying the precipitate from c. to obtain particles, the particles comprising the crystalline form of 4-[(7-methoxy-2,3-dihydro-1,4-benzothiazepin-4(5H)yl) methyl]benzoic acid hemifumarate.

Embodiment 24. A pharmaceutical composition comprising in unit dosage form a crystalline form of 4-[(7-methoxy-2,3-dihydro-1,4-benzothiazepin-4(5H)yl)methyl]benzoic acid hemifumarate, and a pharmaceutically-acceptable excipient, wherein if a melting point of the crystalline form is obtained by:
(a) equilibrating a sample of said crystalline form at a temperature of about 20° C. in a temperature-controlled chamber; and
(b) increasing the temperature of the temperature-controlled chamber at a scan rate of about 10° C./minute to 250° C. using a differential scanning calorimetry instrument,
then a melting point of 201-203° C. ($T_{onset}$) is obtained.

Embodiment 25. The pharmaceutical composition of embodiment 24, wherein the unit dosage form is a solid dosage form.

Embodiment 26. The pharmaceutical composition of embodiment 24 or 25, wherein the unit dosage form is a tablet.

Embodiment 27. The pharmaceutical composition of embodiment 26, wherein the unit dosage form is a gastro-resistant tablet.

Embodiment 28. The pharmaceutical composition of any one of embodiments 24-27, wherein the unit dosage form is suitable for oral administration.

Embodiment 29. The pharmaceutical composition of any one of embodiments 24-28, comprising about 20 mg to about 200 mg of the crystalline form, based on mass of 4-[(7-methoxy-2,3-dihydro-1,4-benzothiazepin-4(5H)yl) methyl]benzoic acid.

Embodiment 30. The pharmaceutical composition of embodiment 29, comprising about 20 mg of the crystalline form, based on mass of 4-[(7-methoxy-2,3-dihydro-1,4-benzothiazepin-4(5H)yl)methyl]benzoic acid.

Embodiment 31. The pharmaceutical composition of any one of embodiments 24-28, comprising about 23.5 mg to about 235 mg of the crystalline form.

Embodiment 32. The pharmaceutical composition of embodiment 31, comprising about 23.5 mg of the crystalline form.

Embodiment 33. A pharmaceutical composition comprising in unit dosage form a crystalline form of 4-[(7-methoxy-2,3-dihydro-1,4-benzothiazepin-4(5H)yl)methyl]benzoic acid hemifumarate, wherein the crystalline form is characterized by a melting point of 201-203° C. ($T_{onset}$), and a pharmaceutically-acceptable excipient.

Embodiment 34. A method of treating a condition, comprising administering to a subject in need thereof a therapeutically-effective amount of a composition, the composition comprising a crystalline form of 4-[(7-methoxy-2,3-dihydro-1,4-benzothiazepin-4(5H)yl)methyl]benzoic acid hemifumarate, wherein if a melting point of the crystalline form is obtained by:
(a) equilibrating a sample of said crystalline form at a temperature of about 20° C. in a temperature-controlled chamber; and
(b) increasing the temperature of the temperature-controlled chamber at about 10° C./minute to 250° C. using a differential scanning calorimetry instrument,
then a melting point of 201-203° C. ($T_{onset}$) is obtained.

Embodiment 35. The method of embodiment 34, wherein the condition is a cardiac condition.

Embodiment 36. The method of embodiment 35, wherein the cardiac condition is characterized by an irregular heartbeat.

Embodiment 37. The method of embodiment 35, wherein the cardiac condition is catecholaminergic polymorphic ventricular tachycardia.

Embodiment 38. The method of embodiment 35, wherein the cardiac condition is heart failure.

Embodiment 39. The method of embodiment 38, wherein the heart failure is congestive heart failure.

Embodiment 40. The method of embodiment 38, wherein the heart failure is chronic heart failure.

Embodiment 41. The method of embodiment 38, wherein the heart failure is heart failure with reduced ejection fraction.

Embodiment 42. The method of embodiment 38, wherein the heart failure is heart failure with preserved ejection fraction.

Embodiment 43. The method of embodiment 38, wherein the subject is a heart failure patient having an implantable cardioverter-defibrillator.

Embodiment 44. The method of embodiment 38, wherein the heart failure is acute heart failure.

Embodiment 45. The method of embodiment 38, wherein the subject is a heart failure patient in need of preservation of cardiac function post myocardial infarction.

Embodiment 46. The method of embodiment 35, wherein the cardiac condition is myocardial infarction.

Embodiment 47. The method of embodiment 35, wherein the cardiac condition comprises cardiac ischemia/reperfusion injury.

Embodiment 48. The method of embodiment 34, wherein the condition is a musculoskeletal condition.

Embodiment 49. The method of embodiment 48, wherein the musculoskeletal condition is a congenital myopathy.

Embodiment 50. The method of embodiment 49, wherein the congenital myopathy is RYR1-related myopathy.

Embodiment 51. The method of embodiment 48, wherein the musculoskeletal condition is a muscular dystrophy.

Embodiment 52. The method of embodiment 51, wherein the muscular dystrophy is Duchenne Muscular Dystrophy.

Embodiment 53. The method of embodiment 48, wherein the musculoskeletal condition is sarcopenia.

Embodiment 54. The method of embodiment 34, wherein the condition is cancer associated muscle weakness.

Embodiment 55. The method of embodiment 54, wherein the cancer associated muscle weakness is cancer cachexia.

Embodiment 56. The method of embodiment 55, wherein the cancer cachexia is due to a cancer having bone metastases.

Embodiment 57. The method of embodiment 34, wherein the condition is diabetes.

Embodiment 58. The method of embodiment 34, wherein the condition is malignant hyperthermia.

Embodiment 59. The method of any one of embodiments 34-58, wherein the therapeutically-effective amount is about 100 mg to about 200 mg per day.

Embodiment 60. The method of any one of embodiments 34-58, wherein the therapeutically-effective amount is about 120 mg per day.

Embodiment 61. The method of any one of embodiments 34-58, wherein the therapeutically-effective amount is about 200 mg per day.

Embodiment 62. A method of treating a condition, comprising administering to a subject in need thereof a therapeutically-effective amount of composition, the composition comprising a crystalline form of 4-[(7-methoxy-2,3-dihydro-1,4-benzothiazepin-4(5H)yl)methyl]benzoic acid hemifumarate, wherein the crystalline form is characterized by melting point of 201-203° C. ($T_{onset}$).

Embodiment 63. A composition comprising a crystalline form of 4-[(7-methoxy-2,3-dihydro-1,4-benzothiazepin-4 (5H)yl)methyl]benzoic acid hemifumarate, for use in a method of treating a condition, wherein if a melting point of the crystalline form is obtained by
(a) equilibrating a sample of said crystalline form at a temperature of about 20° C. in a temperature-controlled chamber; and
(b) increasing the temperature of the temperature-controlled chamber at about 10° C./minute to 250° C. using a differential scanning calorimetry instrument,
then a melting point of 201-203° C. ($T_{onset}$) is obtained.

Embodiment 64. A composition comprising a crystalline form of 4-[(7-methoxy-2,3-dihydro-1,4-benzothiazepin-4 (5H)yl)methyl]benzoic acid hemifumarate, wherein the crystalline form is characterized by a melting point of 201-203° C. ($T_{onset}$), for use in a method of treating a condition.

Embodiment 65. A composition comprising a crystalline form of 4-[(7-methoxy-2,3-dihydro-1,4-benzothiazepin-4 (5H)yl)methyl]benzoic acid hemifumarate, wherein if a melting point of the crystalline form is obtained by:
(a) equilibrating a sample of said crystalline form at a temperature of about 20° C. in a temperature-controlled chamber; and
(b) increasing the temperature of the temperature-controlled chamber at about 10° C./minute to 250° C. using a differential scanning calorimetry instrument,
then a melting point of 208-210° C. ($T_{onset}$) is obtained.

Embodiment 66. The composition of embodiment 65, wherein the crystalline form of 4-[(7-methoxy-2,3-dihydro-1,4-benzothiazepin-4(5H)yl)methyl]benzoic acid hemifumarate is characterized by a differential scanning calorimetry profile substantially as shown in FIG. 7.

Embodiment 67. The composition of embodiment 65 or 66, wherein if an X-ray diffraction pattern of the crystalline form is obtained using measurement conditions, the measurement conditions comprising:

| | |
|---|---|
| Start Position [° 2θ] | 3.00 |
| End Position [° 2θ] | 54.99 |
| Step Size [° 2θ] | 0.018 |
| Scan Step Time [s] | 34.92 |
| Measurement Temperature [° C.] | 25.00 |
| K-Alpha1 [Å] | 1.54 |
| K-Alpha2 [Å] | 1.54 |
| K-Beta [Å] | 1.39 |
| Spinning | Yes | then at least two X-ray diffraction peaks selected from 7.3±0.1, 13.2±0.1, 14.6±0.1, 17.1±0.1, 18.0±0.1, 18.3±0.1, 23.2±0.1, 23.9±0.1, 24.4±0.1, and 28.6±0.1 degrees two theta (°θ) are observed.

Embodiment 68. The composition of embodiment 67, wherein X-ray diffraction peaks at 7.3±0.1, 14.6±0.1, 18.0±0.1, 22.4±0.1, and 24.4±0.1 degrees two theta (°θ) are observed.

Embodiment 69. The composition of embodiment 67 or 68, wherein X-ray diffraction peaks at 7.3±0.1, 11.1±0.1, 14.6±0.1, 18.0±0.1, 19.2±0.1, 22.4±0.1, 23.2±0.1, and 24.4±0.1 degrees two theta (°θ) are observed.

Embodiment 70. The composition of any one of embodiments 67-69, wherein X-ray diffraction peaks at 7.3±0.1, 11.0±0.1, 11.1±0.1, 11.5±0.1, 13.2±0.1, 14.6±0.1, 15.2±0.1, 17.1±0.1, 18.0±0.1, 18.3±0.1, 19.2±0.1, 20.2±0.1, 21.4±0.1, 22.4±0.1, 23.2±0.1, 23.9±0.1, 24.4±0.1 and 28.6±0.1 degrees two theta (°θ) are observed.

Embodiment 71. The composition of any one of embodiments 67-70, wherein X-ray diffraction peaks substantially as shown in FIG. 6 are observed.

Embodiment 72. The composition of any one of embodiments 65-71, wherein if a thermogravimetric analysis of the crystalline form is obtained by:
(a) equilibrating a sample of said crystalline form at 25° C. in a temperature-controlled chamber; and
(b) increasing the temperature at a scan rate of about 10° C./minute to 250° C. using a thermogravimetric analysis instrument
then a thermogravimetric analysis profile substantially as shown in FIG. 8 is obtained.

Embodiment 73. The composition of any one of embodiments 65-72, wherein if a dynamic vapor sorption profile of the crystalline form is obtained by:
(a) equilibrating a sample of said crystalline form at 25° C. and 50% relative humidity in a temperature-controlled and humidity-controlled chamber until mass variation is less than 0.002% per minute for 6 hours;

(b) increasing the relative humidity from 50% to 90% at a rate of 10% per hour;
(c) equilibrating the sample at 90% relative humidity until mass variation of less than 0.002% per minute for 6 hours is observed;
(d) decreasing the relative humidity from 90% to 0% at a rate of 10% per hour;
(e) equilibrating the sample at 0% relative humidity until mass variation of less than 0.002% per minute for 6 hours is observed; and
(f) increasing the relative humidity from 0% to 50% at a rate of 10% per hour, then a dynamic vapor sorption profile substantially as shown in FIG. 9 is obtained.

Embodiment 74. The composition of any one of embodiments 65-73, wherein the crystalline form is substantially anhydrous.

Embodiment 75. The composition of any one of embodiments 65-74, wherein the crystalline form comprises a population of particles, wherein at least about 90% by mass of the particles comprise a diameter of no greater than about 90 microns.

Embodiment 76. The composition of any one of embodiments 65-74, wherein the crystalline form comprises a population of particles, wherein at least about 50% by mass of the particles comprise a diameter of no greater than 30 microns.

Embodiment 77. The composition of any one of embodiments 65-74, wherein the crystalline form comprises a population of particles, wherein at least about 50% by mass of the particles comprise a diameter of between about 10 microns and about 30 microns.

Embodiment 78. A composition comprising a crystalline form of 4-[(7-methoxy-2,3-dihydro-1,4-benzothiazepin-4(5H)yl)methyl]benzoic acid hemifumarate, wherein the crystalline form is characterized by a melting point of 208-210° C. ($T_{onset}$).

Embodiment 79. A composition comprising a crystalline form of 4-[(7-methoxy-2,3-dihydro-1,4-benzothiazepin-4(5H)yl)methyl]benzoic acid hemifumarate, wherein the crystalline form is characterized by an X-ray diffraction pattern comprising least two X-ray diffraction peaks selected from 7.3±0.1, 13.2±0.1, 14.6±0.1, 17.1±0.1, 18.0±0.1, 18.3±0.1, 23.2±0.1, 23.9±0.1, 24.4±0.1, and 28.6±0.1 degrees two theta (°θ).

Embodiment 80. A process for synthesis of a crystalline form of 4-[(7-methoxy-2,3-dihydro-1,4-benzothiazepin-4(5H)yl)methyl]benzoic acid hemifumarate, the process comprising:
a. reacting 4-[(7-methoxy-2,3-dihydro-1,4-benzothiazepin-4(5H)yl)methyl]benzoic acid or an ionized form thereof with fumaric acid in presence of a mixture of dimethyl sulfoxide (DMSO) and water to generate a reaction mixture, the reaction mixture comprising a precipitate;
b. isolating the precipitate from a.;
c. washing the precipitate from b. with water and acetone; and
d. drying the precipitate from c. to obtain particles, the particles comprising the crystalline form of 4-[(7-methoxy-2,3-dihydro-1,4-benzothiazepin-4(5H)yl)methyl]benzoic acid hemifumarate
wherein if a melting point of the crystalline form is obtained by (a) equilibrating a sample of said crystalline form at a temperature of about 20° C. in a temperature-controlled chamber; and (b) increasing the temperature of the temperature-controlled chamber at a scan rate of about 10° C./minute to 250° C., using a differential scanning calorimetry instrument, then a melting point of 208-210° C. ($T_{onset}$) is obtained.

Embodiment 81. The process of embodiment 80, further comprising
(i) cooling the reaction mixture generated in a., wherein (i) is performed prior to b.

Embodiment 82. The process of embodiment 80 or 81, further comprising measuring particle size of the particles comprising the crystalline form of 4-[(7-methoxy-2,3-dihydro-1,4-benzothiazepin-4(5H)yl)methyl]benzoic acid hemifumarate.

Embodiment 83. The process of any one of embodiments 80-82, further comprising reducing the particle size of the crystalline form of 4-[(7-methoxy-2,3-dihydro-1,4-benzothiazepin-4(5H)yl)methyl]benzoic acid hemifumarate.

Embodiment 84. The process of embodiment 83, wherein the crystalline form comprises a population of particles, wherein at least about 90% by mass of the particles comprise a diameter of no greater than about 90 microns.

Embodiment 85. The process of embodiment 83, wherein the crystalline form comprises a population of particles, wherein at least about 50% by mass of the particles comprise a diameter of no greater than about 30 microns.

Embodiment 86. The process of embodiment 83, wherein the crystalline form comprises a population of particles, wherein at least about 50% by mass of the particles comprise a diameter of between about 10 microns and about 30 microns.

Embodiment 87. A process for synthesis of a crystalline form of 4-[(7-methoxy-2,3-dihydro-1,4-benzothiazepin-4(5H)yl)methyl]benzoic acid hemifumarate having a melting point of 208-210° C. ($T_{onset}$), the process comprising:
a. reacting 4-[(7-methoxy-2,3-dihydro-1,4-benzothiazepin-4(5H)yl)methyl]benzoic acid or an ionized form thereof with fumaric acid in presence of a mixture of dimethyl sulfoxide (DMSO) and water to generate a reaction mixture, the reaction mixture comprising a precipitate;
b. isolating the precipitate from a.;
c. washing the precipitate from b. with water and acetone; and
d. drying the precipitate from c. to obtain particles, the particles comprising the crystalline form of 4-[(7-methoxy-2,3-dihydro-1,4-benzothiazepin-4(5H)yl) methyl]benzoic acid hemifumarate.

Embodiment 88. A pharmaceutical composition comprising in unit dosage form a crystalline form of 4-[(7-methoxy-2,3-dihydro-1,4-benzothiazepin-4(5H)yl)methyl]benzoic acid hemifumarate, and a pharmaceutically-acceptable excipient, wherein if a melting point of the crystalline form is obtained by
(a) equilibrating a sample of said crystalline form at 20° C. in a temperature-controlled chamber; and
(b) increasing the temperature of the temperature-controlled chamber at 10° C./minute to 250° C. using differential scanning calorimetry instrument,
then a melting point of 208-210° C. ($T_{onset}$) is obtained.

Embodiment 89. The pharmaceutical composition of embodiment 88, wherein the unit dosage form is a solid dosage form.

Embodiment 90. The pharmaceutical composition of embodiment 88 or 89, wherein the unit dosage form is a tablet.

Embodiment 91. The pharmaceutical composition of embodiment 90, wherein the unit dosage form is a gastro-resistant tablet.

Embodiment 92. The pharmaceutical composition of any one of embodiments 88-91, wherein the unit dosage form is suitable for oral administration.

Embodiment 93. The pharmaceutical composition of any one of embodiments 88-92, comprising about 20 mg to about 200 mg of the crystalline form.

Embodiment 94. The pharmaceutical composition of embodiment 93, comprising about 20 mg of the crystalline form.

Embodiment 95. The pharmaceutical composition of any one of embodiments 88-92, comprising about 23.5 mg to about 235 mg of the crystalline.

Embodiment 96. The pharmaceutical composition of embodiment 95, comprising about 23.5 mg of the crystalline form.

Embodiment 97. A pharmaceutical composition comprising in unit dosage form a crystalline form of 4-[(7-methoxy-2,3-dihydro-1,4-benzothiazepin-4(5H)yl)methyl]benzoic acid hemifumarate, wherein the crystalline form is characterized by a melting point of 208-210° C. ($T_{onset}$), and a pharmaceutically-acceptable excipient.

Embodiment 98. A method of treating a condition, comprising administering to a subject in need thereof a therapeutically-effective amount of a composition, the composition comprising a crystalline form of 4-[(7-methoxy-2,3-dihydro-1,4-benzothiazepin-4(5H)yl)methyl]benzoic acid hemifumarate, wherein if a melting point of the crystalline form is obtained by:
  (a) equilibrating a sample of said crystalline form at a temperature of about 20° C. in a temperature-controlled chamber; and
  (b) increasing the temperature of the temperature-controlled chamber at a scan rate of about 10° C./minute to 250° C. using a differential scanning calorimetry instrument, then a melting point of 208-210° C. ($T_{onset}$) is obtained.

Embodiment 99. The method of embodiment 98, wherein the condition is a cardiac condition.

Embodiment 100. The method of embodiment 99, wherein the cardiac condition is characterized by an irregular heartbeat.

Embodiment 101. The method of embodiment 99, wherein the cardiac condition is catecholaminergic polymorphic ventricular tachycardia.

Embodiment 102. The method of embodiment 99, wherein the cardiac condition is heart failure.

Embodiment 103. The method of embodiment 102, wherein the heart failure is congestive heart failure.

Embodiment 104. The method of embodiment 102, wherein the heart failure is chronic heart failure.

Embodiment 105. The method of embodiment 102, wherein the heart failure is heart failure with reduced ejection fraction.

Embodiment 106. The method of embodiment 102, wherein the heart failure is heart failure with preserved ejection fraction.

Embodiment 107. The method of embodiment 102, wherein the subject is a heart failure patient having an implantable cardioverter-defibrillator.

Embodiment 108. The method of embodiment 102, wherein the heart failure is acute heart failure.

Embodiment 109. The method of embodiment 102, wherein the subject is a heart failure patient in need of preservation of cardiac function post myocardial infarction.

Embodiment 110. The method of embodiment 99, wherein the cardiac condition is myocardial infarction.

Embodiment 111. The method of embodiment 99, wherein the cardiac condition comprises cardiac ischemia/reperfusion injury.

Embodiment 112. The method of embodiment 98, wherein the condition is a musculoskeletal condition.

Embodiment 113. The method of embodiment 112, wherein the musculoskeletal condition is a congenital myopathy.

Embodiment 114. The method of embodiment 113, wherein the congenital myopathy is RYR1-related myopathy.

Embodiment 115. The method of embodiment 112, wherein the musculoskeletal condition is a muscular dystrophy.

Embodiment 116. The method of embodiment 115, wherein the muscular dystrophy is Duchenne Muscular Dystrophy.

Embodiment 117. The method of embodiment 112, wherein the musculoskeletal condition is sarcopenia.

Embodiment 118. The method of embodiment 98, wherein the condition is cancer associated muscle weakness.

Embodiment 119. The method of embodiment 118, wherein the cancer associated muscle weakness is cancer cachexia.

Embodiment 120. The method of embodiment 119, wherein the cancer cachexia is due to a cancer having bone metastases.

Embodiment 121. The method of embodiment 98, wherein the condition is diabetes.

Embodiment 122. The method of embodiment 98, wherein the condition is malignant hyperthermia.

Embodiment 123. The method of any one of embodiments 98-122, wherein the therapeutically-effective amount is about 100 mg to about 200 mg per day.

Embodiment 124. The method of any one of embodiments 98-122, wherein the therapeutically-effective amount is about 120 mg per day.

Embodiment 125. The method of any one of embodiments 98-122, wherein the therapeutically-effective amount is about 200 mg per day.

Embodiment 126. A method of treating a condition, comprising administering to a subject in need thereof a therapeutically-effective amount of composition comprising a crystalline form of 4-[(7-methoxy-2,3-dihydro-1,4-benzothiazepin-4(5H)yl)methyl]benzoic acid hemifumarate, wherein the crystalline form is characterized by melting point of 208-210° C. ($T_{onset}$).

Embodiment 127. A composition comprising a crystalline form of 4-[(7-methoxy-2,3-dihydro-1,4-benzothiazepin-4 (5H)yl)methyl]benzoic acid hemifumarate, for use in treating a condition, wherein if a melting point of the crystalline form is obtained by:
  (a) equilibrating a sample of said crystalline form at 20° C. in a temperature-controlled chamber; and
  (b) increasing the temperature of the temperature-controlled chamber at 10° C./minute to 250° C. using a differential scanning calorimetry instrument, then a melting point of 208-210° C. ($T_{onset}$) is obtained.

Embodiment 128. A composition comprising a crystalline form of 4-[(7-methoxy-2,3-dihydro-1,4-benzothiazepin-4 (5H)yl)methyl]benzoic acid hemifumarate, wherein the crystalline form is characterized by a melting point of 208-210° C. ($T_{onset}$), for use in a method of treating a condition.

Embodiment 129. A pharmaceutical composition comprising a gastro-resistant tablet, the gastro-resistant tablet comprising a crystalline form of 4-[(7-methoxy-2,3-dihydro-1,4-benzothiazepin-4(5H)yl)methyl]benzoic acid hemifumarate as an active ingredient, and a pharmaceutically-acceptable carrier, wherein if a melting point of the crystalline form is obtained by:
  (a) equilibrating a sample of said crystalline form at 20° C. in a temperature-controlled chamber; and
  (b) increasing the temperature of the temperature-controlled chamber at 10° C./minute to 250° C. using a differential scanning calorimetry instrument,
then a melting point of 208-210° C. ($T_{onset}$) is obtained.

Embodiment 130. A method of treating RYR1-related myopathy comprising administering to a subject in need thereof a pharmaceutical composition, wherein the composition comprises a gastro-resistant tablet, the gastro-resistant tablet comprising a therapeutically-effective amount of a crystalline form of 4-[(7-methoxy-2,3-dihydro-1,4-benzothiazepin-4(5H)yl)methyl]benzoic acid hemifumarate, wherein if a melting point of the crystalline form is obtained by:
  (a) equilibrating a sample of said crystalline form at 20° C. in a temperature-controlled chamber; and
  (b) increasing the temperature of the temperature-controlled chamber at 10° C./minute to 250° C. using a differential scanning calorimetry instrument,
  then a melting point of 208-210° C. ($T_{onset}$) is obtained.

Embodiment 131. The method of embodiment 130, wherein the therapeutically-effective amount is about 100 mg to about 200 mg per day.

Embodiment 132. The method of embodiment 130 or 131, wherein the therapeutically-effective amount is about 120 mg per day.

Embodiment 133. The method of embodiment 130 or 131, wherein the therapeutically-effective amount is about 200 mg per day.

Embodiment 134. A method of treating catecholaminergic polymorphic ventricular tachycardia comprising administering to a subject in need thereof a pharmaceutical composition, the pharmaceutical composition comprising a gastro-resistant tablet, the gastro-resistant tablet comprising a therapeutically-effective amount of a crystalline form of 4-[(7-methoxy-2,3-dihydro-1,4-benzothiazepin-4(5H)yl) methyl]benzoic acid hemifumarate, wherein if a melting point of the crystalline form is obtained by:
  (a) equilibrating a sample of said crystalline form at 20° C. in a temperature-controlled chamber; and
  (b) increasing the temperature of the temperature-controlled chamber at 10° C./minute to 250° C. using a differential scanning calorimetry instrument,
  then a melting point of 208-210° C. ($T_{onset}$) is obtained.

Embodiment 135. The method of embodiment 134, wherein the therapeutically-effective amount is about 100 mg to about 200 mg per day.

Embodiment 136. The method of embodiment 134 or 135, wherein the therapeutically-effective amount is about 120 mg per day.

Embodiment 137. The method of embodiment 134 or 135, wherein the therapeutically-effective amount is about 200 mg per day.

Embodiment 138. A pharmaceutical composition comprising a gastro-resistant tablet, the gastro-resistant tablet comprising a therapeutically-effective amount of a crystalline form of 4-[(7-methoxy-2,3-dihydro-1,4-benzothiazepin-4(5H)yl)methyl]benzoic acid hemifumarate as an active ingredient, wherein the crystalline form is characterized by a melting point of 208-210° C. ($T_{onset}$), and a pharmaceutically-acceptable carrier.

Embodiment 139. A method of treating RYR1-related myopathy comprising administering to a subject in need thereof a pharmaceutical composition, the pharmaceutical composition comprising a gastro-resistant tablet, the gastro-resistant tablet comprising a therapeutically-effective amount of a crystalline form of 4-[(7-methoxy-2,3-dihydro-1,4-benzothiazepin-4(5H)yl)methyl]benzoic acid hemifumarate, wherein the crystalline form is characterized by melting point of 208-210° C. ($T_{onset}$).

Embodiment 140. A method of treating catecholaminergic polymorphic ventricular tachycardia comprising administering to a subject in need thereof a pharmaceutical composition, the pharmaceutical composition comprising a gastro-resistant tablet, the gastro-resistant tablet comprising therapeutically-effective amount of a crystalline form of 4-[(7-methoxy-2,3-dihydro-1,4-benzothiazepin-4(5H)yl) methyl]benzoic acid hemifumarate, wherein the crystalline form is characterized by melting point of 208-210° C. ($T_{onset}$).

The invention claimed is:

1. A crystalline form of 4-[(7-methoxy-2,3-dihydro-1,4-benzothiazepin-4(5H)yl)methyl]benzoic acid hemifumarate, wherein if a melting point of the crystalline form is obtained by:
  (a) equilibrating a sample of said crystalline form at a temperature of about 20° C. in a temperature-controlled chamber; and
  (b) increasing the temperature of the temperature-controlled chamber at about 10° C./minute to 250° C. using a differential scanning calorimetry instrument,
then a melting point of 208-210° C.($T_{onset}$) is obtained.

2. The crystalline form of claim 1, wherein the crystalline form of 4-[(7-methoxy-2,3-dihydro-1,4-benzothiazepin-4 (5H)yl)methyl]benzoic acid hemifumarate is characterized by a differential scanning calorimetry profile substantially as shown in FIG. 7.

3. The crystalline form of claim 1, wherein if a thermogravimetric analysis of the crystalline form is obtained by:
  (a) equilibrating a sample of said crystalline form at 25° C. in a temperature-controlled chamber; and
  (b) increasing the temperature at a scan rate of about 10° C./minute to 250° C. using a thermogravimetric analysis instrument,
then a thermogravimetric analysis profile substantially as shown in FIG. 8 is obtained.

4. The crystalline form of claim 1, wherein if a dynamic vapor sorption profile of the crystalline form is obtained by:
  (a) equilibrating a sample of said crystalline form at 25° C. and 50% relative humidity in a temperature-controlled and humidity-controlled chamber until mass variation is less than 0.002% per minute for 6 hours;
  (b) increasing the relative humidity from 50% to 90% at a rate of 10% per hour;
  (c) equilibrating the sample at 90% relative humidity until mass variation of less than 0.002% per minute for 6 hours is observed;
  (d) decreasing the relative humidity from 90% to 0% at a rate of 10% per hour;
  (e) equilibrating the sample at 0% relative humidity until mass variation of less than 0.002% per minute for 6 hours is observed; and
  (f) increasing the relative humidity from 0% to 50% at a rate of 10% per hour,
then a dynamic vapor sorption profile substantially as shown in FIG. 9 is obtained.

5. The crystalline form of claim 1, wherein the crystalline form is substantially anhydrous.

6. The crystalline form of claim 1, wherein the crystalline form comprises a population of particles, wherein at least about 90% by mass of the particles comprise a diameter of no greater than about 90 microns.

7. The crystalline form of claim 1, wherein the crystalline form comprises a population of particles, wherein at least about 50% by mass of the particles comprise a diameter of no greater than 30 microns.

8. The crystalline form of claim 1, wherein the crystalline form comprises a population of particles, wherein at least about 50% by mass of the particles comprise a diameter of between about 10 microns and about 30 microns.

9. A pharmaceutical composition comprising in solid unit dosage form a crystalline form of 4-[(7-methoxy-2,3-dihydro-1,4-benzothiazepin-4(5H)yl)methyl]benzoic acid hemifumarate, wherein if a melting point of the crystalline form is obtained by:
 (a) equilibrating a sample of said crystalline form at 20° C. in a temperature-controlled chamber; and
 (b) increasing the temperature of the temperature-controlled chamber at 10° C. /minute to 250° C. using a differential scanning calorimetry instrument,
then a melting point of 208-210° C. ($T_{onset}$) is obtained.

10. The pharmaceutical composition of claim 9, wherein the unit dosage form is a tablet.

11. The pharmaceutical composition of claim 9, wherein the unit dosage form is a gastro-resistant tablet.

12. The pharmaceutical composition of claim 9, wherein the unit dosage form is suitable for oral administration.

13. The pharmaceutical composition of claim 9, further comprising a pharmaceutically-acceptable excipient.

14. A method of treating a condition, comprising administering to a subject in need thereof a therapeutically-effective amount of a crystalline form of 4-[(7-methoxy-2,3-dihydro-1,4-benzothiazepin-4(5H)yl)methyl]benzoic acid hemifumarate, wherein if a melting point of the crystalline form is obtained by:
 (a) equilibrating a sample of said crystalline form at a temperature of about 20° C. in a temperature-controlled chamber; and
 (b) increasing the temperature of the temperature-controlled chamber at a scan rate of about 10° C./minute to 250° C. using a differential scanning calorimetry instrument,
then a melting point of 208-210° C. ($T_{onset}$) is obtained, wherein the condition is catecholaminergic polymorphic ventricular tachycardia, heart failure, muscular dystrophy, or malignant hyperthermia.

15. The method of claim 14, wherein the condition is catecholaminergic polymorphic ventricular tachycardia.

16. The method of claim 14, wherein the condition is heart failure.

17. The method of claim 14, wherein the condition is a muscular dystrophy.

18. The method of claim 17, wherein the muscular dystrophy is Duchenne Muscular Dystrophy.

19. The method of claim 14, wherein the condition is malignant hyperthermia.

20. The method of claim 14, wherein the therapeutically-effective amount is about 100 mg to about 200 mg per day.

21. The method of claim 14, wherein the therapeutically-effective amount is about 200 mg per day.

22. The method of claim 14, wherein the therapeutically-effective amount is about 300 mg per day.

23. The method of claim 14, wherein the therapeutically-effective amount is about 400 mg per day.

24. A pharmaceutical composition comprising a gastro-resistant tablet, the gastro-resistant tablet comprising a crystalline form of 4-[(7-methoxy-2,3-dihydro-1,4-benzothiazepin-4(5H)yl)methyl]benzoic acid hemifumarate as an active ingredient, and a pharmaceutically-acceptable carrier, wherein if a melting point of the crystalline form is obtained by:
 (a) equilibrating a sample of said crystalline form at 20° C. in a temperature-controlled chamber; and
 (b) increasing the temperature of the temperature-controlled chamber at 10° C./minute to 250° C. using a differential scanning calorimetry instrument,
then a melting point of 208-210° C. ($T_{onset}$) is obtained.

25. A method of treating catecholaminergic polymorphic ventricular tachycardia comprising administering to a subject in need thereof a pharmaceutical composition according to claim 24.

* * * * *